(12) United States Patent
Tajima

(10) Patent No.: US 8,486,347 B2
(45) Date of Patent: Jul. 16, 2013

(54) CARRIER-ENCLOSED TRANSFORMABLE CONTAINER, CARRIER-ENCLOSED TRANSFORMABLE CONTAINER PROCESSING APPARATUS, AND CARRIER-ENCLOSED TRANSFORMABLE CONTAINER PROCESSING METHOD

(75) Inventor: Hideji Tajima, Matsudo (JP)

(73) Assignee: Universal Bio Research Co., Ltd., Matsudo-Shi, Chiba (JP)

( * ) Notice: Subject to any disclaimer, the term of this patent is extended or adjusted under 35 U.S.C. 154(b) by 873 days.

(21) Appl. No.: 12/304,596

(22) PCT Filed: Jun. 12, 2007

(86) PCT No.: PCT/JP2007/061805
§ 371 (c)(1),
(2), (4) Date: Sep. 24, 2009

(87) PCT Pub. No.: WO2007/145206
PCT Pub. Date: Dec. 21, 2007

(65) Prior Publication Data
US 2010/0015010 A1    Jan. 21, 2010

(30) Foreign Application Priority Data
Jun. 13, 2006   (JP) .................................. 2006-164042

(51) Int. Cl.
*B01L 3/02* (2006.01)

(52) U.S. Cl.
USPC ........... 422/501; 422/69; 422/509; 73/864.11

(58) Field of Classification Search
USPC ...... 422/501, 509–517, 69; 435/287.1–288.7; 436/518–535, 178, 180; 73/864.01–864.25
See application file for complete search history.

(56) References Cited

U.S. PATENT DOCUMENTS
4,296,071 A * 10/1981 Weiss et al. ................. 73/864.11
4,784,834 A * 11/1988 Hirschmann ................. 422/517
(Continued)

FOREIGN PATENT DOCUMENTS
JP   37713/1971   5/1971
JP   64-17333   1/1989
(Continued)

OTHER PUBLICATIONS

English Translation of International Search Report, International Application No. PCT/JP2007/061805, Sep. 11, 2007; 4 pgs; Japanese Patent Office.

(Continued)

*Primary Examiner* — Jan Ludlow
(74) *Attorney, Agent, or Firm* — Haynes and Boone, LLP

(57) ABSTRACT

Provided are a carrier-enclosed transformable container, a carrier-enclosed transformable container processing apparatus, and a carrier-enclosed transformable container processing method about which a carrier to which various substances such as biogenic substances are bonded or bondable is held in a transformable container as the container to be in a substantially stationary state, thereby making it possible to make the handling of the carrier, measurement, and other treatments effective, speedy, and easy. The container is formed to have: a containing part which can contain liquid and gas at its inside surrounded by a wall face, a part of this wall face having a transformable wall face capable of undergoing a predetermined transformation without changing the entire internal surface area of the wall face substantially; an orifice part which is connected to the containing part and can undergo the inflow and outflow of a liquid sucked and discharged by the expansion and contraction of the inside by the transformation of the transformable wall face, respectively; and a carrier to which a predetermined substance enclosed in the containing part to be in a substantially stationary state is bonded or bondable.

14 Claims, 14 Drawing Sheets

U.S. PATENT DOCUMENTS

| | | | |
|---|---|---|---|
| 4,999,286 A * | 3/1991 | Gawel et al. | 435/7.32 |
| 5,055,271 A | 10/1991 | Golias | |
| 5,173,265 A | 12/1992 | Golias | |
| 5,406,856 A * | 4/1995 | Kuhn | 73/864.14 |
| 5,525,302 A * | 6/1996 | Astle | 422/511 |
| 5,844,686 A * | 12/1998 | Treptow et al. | 356/440 |
| 5,895,631 A | 4/1999 | Tajima | |
| 6,133,037 A * | 10/2000 | Tajima | 436/49 |
| 6,509,193 B1 | 1/2003 | Tajima | |
| 6,660,233 B1 * | 12/2003 | Coassin et al. | 422/564 |
| 2002/0007054 A1 | 1/2002 | Sakurai | |
| 2002/0094565 A1 | 7/2002 | Sakurai | |
| 2005/0124058 A1 | 6/2005 | Tajima | |
| 2005/0282182 A1 | 12/2005 | Tajima | |
| 2006/0084131 A1 | 4/2006 | Nakayama et al. | |

FOREIGN PATENT DOCUMENTS

| | | |
|---|---|---|
| JP | 1-10578 Y2 | 3/1989 |
| JP | 05-256859 | 10/1993 |
| JP | 08-062224 | 3/1996 |
| JP | 11-502937 | 3/1999 |
| JP | 11-266864 | 10/1999 |
| JP | 2000-346842 | 12/2000 |
| JP | 2004-301715 | 10/2004 |
| WO | WO96/29602 | 9/1996 |
| WO | WO9744671 | 11/1997 |
| WO | WO99/58955 | 11/1999 |
| WO | WO01/53831 | 7/2001 |
| WO | WO03/060115 | 7/2003 |
| WO | WO2005/064334 | 7/2005 |
| WO | WO2007/145206 | 12/2007 |

OTHER PUBLICATIONS

English Translation of International Preliminary Report on Patentability Chapter II, International Application No. PCT/JP2007/061805; 6 pgs; Japanese Patent Office.

Written Opinion of the International Searching Authority, International Application No. PCT/JP2007/061805; Sep. 11, 2007; 6 pgs; Japanese Patent Office.

* cited by examiner

CARRIER-ENCLOSED TRANSFORMABLE CONTAINER, CARRIER-ENCLOSED TRANSFORMABLE CONTAINER PROCESSING APPARATUS, AND CARRIER-ENCLOSED TRANSFORMABLE CONTAINER PROCESSING METHOD

CROSS REFERENCE

This application is a United States national phase application of co-pending international patent application number PCT/JP2007/061805, filed Jun. 12, 2007, which claims priority to Japanese patent application number 2006-164042, filed Jun. 13, 2006, the disclosures of which are incorporated herein by reference.

TECHNICAL FIELD

The present invention relates to a carrier-enclosed transformable container, a carrier-enclosed transformable container processing apparatus, and a carrier-enclosed transformable container processing method.

BACKGROUND ART

Conventionally, in the case of conducting a series of reaction treatments using a large number of reagents or substances for a target material which is an object to be examined, for example, the target material is bonded to a minute carrier made of beads or the like and then the resultant is incorporated into a test tube. Thereafter, various ones of the reagents or substances are injected to the test tube to separate the carrier in some manner. The carrier is then moved to a different container, and further different ones of the reagents or substances are injected thereto or are subjected to heating treatment or some other treatment. In a case where the carrier is, for example, a magnetic substance, the separation is attained by causing the carrier to be adsorbed onto the inner wall of the test tube by a magnetic field.

About the processing of using a planar carrier, such as a prepared slide, to which, for example, various oligonucleotides are fixed to examine a target material, the base sequence structure of the target material is examined by conducting a series of reaction treatments, such as a treatment of moving the carrier itself into a suspension wherein the target material that has been marked is suspended, a treatment of partitioning various reagents into the carrier itself, a treatment of moving the carrier itself into a washing solution, and a treatment of moving the carrier to a measuring position of a measuring device in order to measure light emitted therefrom.

In order to conduct these treatments, it is necessary to separate the carrier itself and move the carrier itself. Thus, there remain problems that the treatments are complicated and require much time and labor. In particular, in the case of moving such carriers themselves, much burden is imposed to users when the movement is manually attained. Moreover, cross-contamination may be caused. In the case of moving the carriers themselves mechanically, a large-scaled apparatus is necessary. In the case of separating the carrier of a nonmagnetic type, there is a problem that the separation needs to be attained by aid of the size or specific gravity of the carrier so that the treatment is complicated and requires much time and labor.

Thus, an apparatus using a partitioning device invented by the present inventors without using any test tube or planar carrier is known, the apparatus having a pipette chip having a liquid-passing path through which liquid can pass, a nozzle to which the pipette chip is fitted, a magnetizing device for applying a magnetic field to the liquid-passing path of the pipette chip, and a sucking and discharging mechanism including a cylinder having therein a plunger for sucking and discharging a fluid into/from the pipette chip.

According to this method, a suspension wherein many magnetic particles having surfaces which hold various substances are suspended is sucked, and a magnetic field is applied thereto at the time of the suction, whereby the magnetic particles are effectively caused to be adsorbed to the liquid-passing path of the pipette chip, so as to attain separation thereof or the like. However, the magnetic particles can pass through the liquid-passing path; it is therefore necessary to apply a magnetic field to the magnetic particles so as to cause the particles to be adsorbed on the inner wall in order that the pipette chip can hold therein the magnetic particles. It is therefore necessary to combine the control of suction and discharge, the control of adsorption through the magnetic field, and the moving control of the pipette chip with each other in order to conduct the processing. In a case where the carrier is made of nonmagnetic particles, there also remains a problem that the carrier cannot be separated by means of the apparatus.

Furthermore, the cylinder for driving the plunger is used as the sucking and discharging mechanism, and the plunger or some other similar mechanism is a highly-precise worked member such as a syringe. In particular, the volume change of the inside of the cylinder unifies basically with the volume change of the inside of the partitioning chip; thus, it is necessary to transmit the change so as not to loosen a jointing region between the plunger and the driving device for the plunger. It is also necessary to fit the nozzle of the sucking and discharging mechanism to the partitioning chip or the like without leaking off air or liquid. Thus, precision and structure for attaining watertightness or airtightness are required for production or quality-control. In particular, in a case where plural partitioning chips are integrated with each other and used, a large force is required for inserting and fitting plural nozzles into the portioning chips simultaneously so as to be set thereto. As a result, O rings, which are members for keeping watertightness and airtightness, may be severely worn away. Thus, a high-level quality control may be required.

In the case of fitting plural partitioning chips to nozzles of the sucking and discharging mechanism while exchanging the chips, so as to conduct treatments continuously, it is necessary to prevent cross-contamination by the contact between the nozzles and gas or liquid in the partitioning chips.

Furthermore, in order to control the suction and the discharge of the partitioning chips, cylinders having a volume consistent with the volume of the partitioning chips are required; thus, in order to handle a liquid having a large volume, there arises a problem that the scale of the apparatus becomes large (Patent Documents 1 to 3).

Known is also a method of holding beads with probes in small holes and then moving the beads into a capillary or groove to arrange the beads in a predetermined order in accordance with the kinds of the beads to produce a probe bead array, or causing beads with probes to flow in a liquid flow in a predetermined order and then putting the beads into a groove or capillary to produce a probe array having array pieces arranged in a predetermined order (Patent Document 4).

Furthermore, as a system or method for detecting many substances to be analyzed in a fluid sample, and analyzing the substances at real time to display the results, known is a system or method having at least one light source, at least one photodetector, optical assemblies on substantially the same plane, and a memory medium that can communicate with a computer, can be read by the computer and can store commands from the computer, wherein one of the commands includes a treatment of some biological sample, using a flow cytometer, and a decision of the existence and the amount of at least one interested substance to be analyzed in the biological sample, the treatment and the decision being simultaneously conducted (Patent Document 5).

However, particles are very small (for example, from several tens of micrometers to several millimeters) for being handled by persons; therefore, there is a problem that in order to arrange many particles in a predetermined order into a groove or capillary precisely, much labor and time are necessary, and the operation for the arrangement is difficult. There is also a problem that the arrangement of the particles gets out of position so that the particles cannot be matched with precise positions. Additionally, in the case of using the flow cytometer to move particles suspended in a liquid at a high speed and measuring the particles with the photodetector, it is necessary to trace the particles one by one strictly, and measure the particles. Thus, there remains a problem that the structure of the apparatus may become complicated or complicated control may become necessary.

[Patent Document 1] Japanese Patent No. 3115501
[Patent Document 2] Internal Publication WO 96/29602
[Patent Document 3] Internal Publication WO 97/44671
[Patent Document 4] Japanese Patent Application Laid-Open (JP-A) No. 2000-346842
[Patent Document 5] Japanese Patent Application National Publication No. 14-534657

PROBLEMS TO BE SOLVED BY THE INVENTION

Thus, a first object of the invention is to provide a carrier-enclosed transformable container, a carrier-enclosed transformable container processing apparatus, and a carrier-enclosed transformable container processing method about which a carrier to which various substances such as biological substance are bonded or bondable is enclosed into a transformable container as the container to be in a substantially stationary state, thereby making it possible to make the handling, the measurement and other treatments of the carrier effective, speedy and easy.

A second object of the invention is to provide a carrier-enclosed transformable container, a carrier-enclosed transformable container, a carrier-enclosed transformable container processing apparatus, and a carrier-enclosed transformable container processing method about which a transformable container as the container is used to make it possible to conduct automatically or manually a series of treatments of various substances, such as the movement, reaction and measurement thereof, to the last in the transformable container, and further prevent cross-contamination based on contact between liquid introduced into the container and a substance outside the container as much as possible.

A third object of the invention is to provide a carrier-enclosed transformable container, a carrier-enclosed transformable container processing apparatus, and a carrier-enclosed transformable container processing method about which a transformable container as the container is used to make it possible to bring a liquid having a large volume (for example, from one milliliter (cc) to several tens of millimeters) into contact with a carrier through structure relatively small in apparatus-scale, and further process a liquid having an ordinary volume (for example, from several tens of microliters to several hundreds of microliters).

A fourth object of the invention is to provide a carrier-enclosed transformable container, a carrier-enclosed transformable container processing apparatus, and a carrier-enclosed transformable container processing method about which a highly precise processing can be attained without using any complicated fluid mechanism although a simple device structure, which is a transformable container as the container, is used.

A fifth object of the invention is to provide a carrier-enclosed transformable container, a carrier-enclosed transformable container processing apparatus, and a carrier-enclosed transformable container processing method which can each be supplied at low costs and can be decreased in controlling-burden, without precision for watertightness, airtightness or the like being required for production or quality control, by using a transformable container as the container.

A first aspect of the invention is a product having a containing part which can contain liquid and gas at its inside surrounded by a wall face, a part of this wall face having a transformable wall face capable of undergoing a predetermined transformation without changing the entire internal surface area of the wall face substantially; an orifice part which is connected to the containing part and can undergo the inflow and outflow of a liquid sucked and discharged by the expansion and contraction of the inside by the transformation of the transformable wall face, respectively; and a carrier to which a predetermined substance enclosed in the containing part to be in a substantially stationary state is bonded or bondable.

The "transformable wall face" is a flexible wall face, which is transformable, and is further a wall face having a surface area substantially unchanged by the transformation thereof. In other words, the surface area of the wall face is substantially maintained before and after the transformation. Examples thereof include a case where a collapsed wall face is transformed to be extended, and a case where a loosened wall face is transformed to be turned into a strain state. Accordingly, even the wall face into which the transformable wall face is incorporated has a total surface area unchanged by the transformation. The wording "a part of this wall face" denotes, for example, the wall face portion other than the vicinity of the orifice part in the entire wall face of the containing part. Between the wall face portion and the orifice part is arranged a non-transformable wall face, which is not transformable.

The "predetermined transformation" of the transformable wall face is preferably a transformation permitting the internal volume to be substantially specified in accordance with the degree of an applied transformation force. In other words, it is preferred that the inside surrounded by the wall face is expanded or contracted in accordance with such a degree that the transformable wall face is pushed or pulled along some transformable direction or the force therefor is removed, so that the volume of the inside is uniformly decided.

The transformable wall face may be urged in the direction of the expansion or contraction of the inside by the transformation thereof. When the face is urged in the expansion direction, the wall is contracted by applying force oppositely to the expansion direction and the wall is transformed in the expansion direction by removing the force. When the face is urged in the contraction direction, the wall is expanded by applying force oppositely to the contraction direction and the wall is transformed in the contraction direction by removing the force. The transformable wall face is, for example, a wall face that a flexible plane-form member or membrane-form member forms, examples thereof including a wall face wherein a bellow is formed, or a wall face which a plane-form member or membrane-form member of an elastomer such as rubber forms or a wall face which contains therein a spring or some other member giving elastic force along the transformable direction.

The wording "sucked and discharged" has a meaning of being sucked and/or discharged. Examples of the material of the carrier-enclosed transformable container include resins such as polystyrene, polysulfone, polyethylene, polypropylene, polyester, polyvinyl, and acrylic resin; elastomers such as rubber; other flexible materials; and combinations thereof. The carrier-enclosed transformable container is preferably transparent or semitransparent. The non-transformable wall face is made of, for example, polypropylene, and the transformable wall face is made of, for example, polyethylene.

About the size of the carrier-enclosed transformable container, the length thereof along the direction from the orifice part to the fitting opening or in the axial direction thereof is, for example, from several centimeters to several tens of centimeters, and the volume thereof is, for example, from several microliters to several tens of milliliters in accordance with the length. The sucking and discharging amount is, for example, from several microliters to several tens of milliliters in accordance with the volume.

The word "enclosed" means that a substance (for example, a carrier) put in a container having an orifice part capable of undergoing the inflow and the outflow of liquid is held in such a manner that the substance does not flow out through the orifice part.

The wording "in a substantially stationary state" means that the carrier is in a state substantially immovable between individuals of the carrier or relatively to an introduced liquid in the containing part at the time of being measured, so as to be measurable. However, it is not necessarily essential that the carrier is in a completely fixed state.

The "carrier to which a predetermined substance is bonded or bondable" is a solid to which a predetermined substance is bonded or bondable, the solid being enclosed in the containing part. The carrier is made of, for example, a porous material, an organic substance such as a resin holding a given functional group or given compound, a fibrous material or some other natural substance; or an inorganic substance such as a metal, a semiconductor, a glass, or silica. The shape of the carrier may be, for example, a particulate shape, linear shape, rodlike shape, planar shape, or block shape. Examples of the "predetermined substance" include genetic materials, such as nucleic acids such as DNA and RNA and oligonucleotide; various compounds, such as proteins such as immunity substances, peptides, amino acids, sugar, sugar chains and other biogenic compounds; and living bodies themselves and biogenic tissues, such as cells, bacteria, viruses, and plasmids. The "predetermined substance" may be made of a singe species or plural species. The biogenic compounds are each used for detecting a bond of another biogenic compound, as a receptor, having bondability to the biogenic compound as a ligand, and attaining capturing, separation, extraction or the like. The following fall under the receptor: genetic materials, such as the above-mentioned nucleic acids; genetic materials such as nucleic acids each having bondability to a protein, a sugar chain, a peptide or the like; and biogenic substances such as proteins, sugar chains, and peptides. A living body itself, such as a cell, a virus or a plasmid, may be used as one of the biogenic compounds or instead of any one of the biogenic compounds. To the carrier is fixed the predetermined substance, such as a material which has or appears to have bondability to a ligand or a receptor, an example of the material being a receptor or a ligand, respectively.

The word "bonded" or "bond" means that at least one species of the predetermined substance is caused to be related to the carrier directly or through a different substrate. Examples of the bond include a covalent bond, a bond based on chemical adsorption, and a bond based on physical adsorption, hydrogen bonding or electrical interaction. The predetermined chemical substance is bonded to the carrier through chemical or physical adsorption, a specific reaction with a bonding material fixed and set to the carrier, or some other method. The carrier may be formed by a porous member, an irregularity (or unevenness)-formed member, or a fibrous member, thereby heightening the reacting power or bonding power thereof to a biogenic substance or the like.

Examples of the material of the "carrier" include inorganic substances, such as metals, semiconductors, semi-metals, metal compounds such as metal oxides, ceramics, glasses, and silica; and organic substances, such as resins such as rubber, latex, polystyrene, polypropylene, polyester and acrylic resins, polymeric materials such as cellulose, the above-mentioned nylon and other fibrous materials, and natural substances such as silk and other natural fibers. Specific examples of the fibrous materials include silk and nylons (3-nylon, 6-nylon, 6,6-nylon, 6,10-nylon, 7-nylon and 12-nylon) each made of a "polyamide polymer", entire aromatic polyamides such as PPTA (polyparaphenylene terephthalamide), and hetero-ring-containing aromatic polymers. The carrier may be, for example, a fibrous body, a porous body or a gelatinous body.

For the bonding, a functional group is caused to be expressed or generated in the carrier. For this purpose, the peptide bond which a "polyamide polymer" has is hydrolyzed, thereby causing a functional group that is to be used for bonding to a biogenic substance to be expressed or generated. Examples of the functional group, which bondable to a biogenic substance, include a carboxyl group —COOH, an amino group —$NH_2$, and groups derived therefrom. The diameter of the pores suitable for being bonded to a biogenic compound is, for example, several micrometers or less.

The "carrier" is a solid which is made of one or more individuals in a solid state (each) having a size permitting the individual(s) to be enclosed in the carrier-enclosed transformable container, and which makes the following possible: positions where the predetermined substance is bonded or bondable are specified from the outside of the carrier-enclosed transformable container. In order to attain the bonding of the predetermined substance or make this bonding possible, the carrier is enclosed into the container as follows: the bonding positions or bondable positions are caused to correspond to predetermined positions of an individual of the carrier at intervals, or to correspond to predetermined individuals of the carrier so that, for example, the bonding positions or the bondable positions can be specified, for example, through a one-dimensional coordinate along the axial direction of the carrier-enclosed transformable container, or in a random state. Examples of the carrier include one or more carrier particles, carrier shapers, carrier lines, carrier rods, carrier stripes, and carrier planes, and carrier blocks and the like.

In the case, the structure and the nature of a target biogenic substance, or whether or not the substance is present can be analyzed by bringing a solution containing a predetermined marked substance into contact with the carrier in the above-mentioned chip-form container, thereby measuring whether or not a bond to the biogenic substance is present by measuring light emitted from the individual positions. Herein, the predetermined marked substance is marked with a marking substance which is a luminescent substance, such as a fluorescent substance which is fixed to the carrier or bondable to the carrier itself.

About the size of the transformable container, the between-intersection-length or the axial-direction-length between the transformable wall face and the orifice part, along a straight line passing through the orifice part and surrounded by the containing part, is, for example, from several centimeters to several tens of centimeters, and the volume thereof is from approximately several microliters to several tens of milliliters in accordance with the length.

A second aspect of the invention is the carrier-enclosed transformable container wherein the containing part has one or more transformable portions formed by the transformable wall face, and a non-transformable portion connected to the transformable portion(s), surrounded by a non-transformable wall face, which is not transformable, and connected to the orifice part, the inside of the non-transformable portion being permitted to be measured from the outside; and the carrier is enclosed in the non-transformable portion.

The transformable portion(s) formed by the transformable wall face is/are one or more portions which undergo the application of an external force, so as to be transformed. The transformable portion(s) may be single or plural.

The wording "being permitted to be measured from the outside" means that the state that individual carrier particles held in the portion where the carrier is to be held are marked can be specified from the outside.

A third aspect of the invention is the carrier-enclosed transformable container wherein the containing part has at least two of the transformable portions, and is formed to make the following different from each other: maximum variable volumes based on transformations of the transformable wall faces of the individual transformable portions.

One of the maximum variable volumes at least two of the transformable portions is made substantially equal to the volume of a thin-tube portion in which the carrier is enclosed or the volume of a region in which the carrier is enclosed, whereby the carrier can be effectively brought into contact with a liquid required to be brought into contact with the carrier, for example, a reagent solution or a specimen suspension by preparing a minimum necessary amount of the liquid in the container and using the transformable portion to transform the container. About a washing liquid therefor, the other transformable portion(s) is/are used to bring the liquid into contact with not only the thin-tube portion, in which the carrier is enclosed, but also a thick-tube portion. In this way, liquids having at least two volumes different from each other can be sucked or discharged. In particular, in the case of handling the container by hand, the exchanges of the volumes can be attained not by adjusting the magnitude of force applied to the transformable portions but by selecting one(s) of the transformable portions.

A fourth aspect of the invention is the carrier-enclosed transformable container wherein the transformable portion the maximum variable volume of which is the largest, or the only one transformable portion is formed to make its transformable wall face transformable at intersections between the transformable wall face and a straight line passing through the insides of the orifice part and the containing part to penetrate the transformable wall face, and along the straight line.

A fifth aspect of the invention is the carrier-enclosed transformable container wherein the carrier is made of plural carrier particles or plural carrier particle groups to which plural chemical substances (=plural chemical substance species) are bonded or bondable, the particles or the groups being capable of being distinguished from the outside.

The "carrier particles" are solid particles each having a size permitting the particle to be introduced and held in the above-mentioned carrier holding portion. Usually, any one individual of the carrier particles or any one group of the carrier particle groups corresponds to one of the chemical substances which are bonded or bondable thereto. About the size of the carrier particles, the diameter thereof is, for example, from 0.1 mm to several millimeters. About the volume of the spatial portion in which the carrier particles are enclosed, the spatial portion other than the enclosed carrier particles has, for example, a volume of several microliters to several hundreds of microliters. In the case of marking the carrier particles or the carrier particle groups correspondingly to the bonded or bondable chemical substances, the particles or groups do not need to be distinguished dependently on the arrangement positions of the enclosed carrier particles or the groups thereof.

The "carrier particle groups" are each a particulate carrier group to which at least two carrier particles belong. The carrier particles belonging to the group are specified by a predetermined particle number, a predetermined distance between the carrier particles belonging thereto, a predetermined range wherein the carrier particles are positioned, or a predetermined boundary, coat film or case which surrounds the carrier particles belonging thereto. As a result thereof, the carrier particle group can be handled together as if they were a single carrier particle. Functions may be dispersed in each of the particles, examples of the function-dispersed particles including carrier particles having functions of immobilizing various substances, carrier particles having a function of attaining discrimination or identification, and other carrier particles (for showing boundaries between the groups, or shielding light or the like not to mix light rays or the like generated by the marking with each other), whereby the handling of the carrier particles can be made easy and further other various functions can be added thereto. When a group can be clearly identified even as a group of carrier particles, the number of the carrier particles belonging thereto can be freely set; thus, the aspect of the invention is expandable, versatile, and variable.

A sixth aspect of the invention is the carrier-enclosed transformable container wherein individuals of the carrier particles, or individual carrier particles of at least one group belonging to the individual carrier particle groups are marked to be distinguishable from each other correspondingly to the kinds of the chemical substances, the individuals of the carrier particles, or the individual carrier particle groups before the individuals are introduced into the containing part.

The "individuals of the carrier particles, or the individual carrier particles of at least one group belonging to the individual carrier particle groups are marked to be distinguishable from each other correspondingly to the kinds of the chemical substances, the individuals of the carrier particles, or the individual carrier particle groups"; therefore, it is unnecessary that they are introduced and held in the carrier holding portion to form an array, and become distinguishable from each other first from positional data thereof.

The wording "the carrier particles are marked to be distinguishable" means that distinguishable marking elements are held by the carrier particles themselves or are bonded or fixed thereto, or the carrier particles themselves can be worked or formed to be distinguishable. In other words, the cause of the marking is present in the carrier particles, and this matter is different from a case where the cause of the marking is present outside the carrier particles, an example of the outside cause being the arrangement or the position of the carrier particles. The marking is attained, for example, by making the shape of the carrier particles spherical, cubic, columnar, prismatic, conical or pyramidal, giving irregularities to the carrier particles, making the sizes of the carrier particles into many variations, attaching various dyes to the carrier particles, and fitting, to carrier particles, marking elements, for example, various luminescent substances such as fluorescent substances, phosphorescent substances or chemically luminescent substances, radiating substances which emit electromagnetic waves having various wavelengths, for example, infrared rays, ultraviolet rays and electric waves having various wavelengths, or magnetic bodies having various magnetization intensities. For the marking in the case, the marking elements, such as the luminescent substances, the various electromagnetic-wave-radiating substances or the magnetic bodies, may be fitted to the surfaces of the carrier particles, or may be fitted to the insides of the carrier particles. An example of the latter case is a case of particulate cases or particulate coats wherein the carrier particles are made hollow and the above-mentioned substances are incorporated or bundled into the hollows. In the case, it is necessary that the particulate cases or particulate coats in the case of the luminescent substances are transparent or semitransparent. The carrier particles have the marking elements or the carrier particles themselves are worked or formed to be distinguishable before the carrier particles are introduced and held in the carrier holding portion.

The marking elements may be bonding substances which can each react specifically with a predetermined luminescent substance or the like distinguishable by measurement, and is not yet in a state unreacted with the luminescent substance or the like. An example of such a bonding substance is a receptor having bondability to a ligand bonded to the luminescent substance or the like. This marking element is latently marked; thus, the element is caused to react with the predetermined luminescent substance or the like to express a visible mark. Accordingly, when this marking element is used, the carrier particles are latently marked to be distinguishable from each other before the particles are introduced into the carrier holding portion. By reaction after the introduction, a visible mark is expressed. Such a case is also included in the case where the carrier particles are marked before the introduction.

In this way, about the carrier particles distinguishable from each other, the various substances fixed or fixable to the carrier particles can be recognized by distinguishing the individual carrier particles or the individual carrier particle groups without arranging the carrier particles to be distinguishable about their positions, or moving the carrier particles or changing the order thereof. Accordingly, for example, in the case of bringing the carrier particles into contact with a suspension of a target substance marked by a different method for causing reaction or bonding to the various substances, the various substances to which the target substance is bonded can be specified on the basis of a combination of the marking of the target substance with the marking of the carrier particles.

In short, according to the invention, the individual carrier particles make it possible to cause various substance which the carrier particles fix or can fix to be recognized even by keeping the positions or the order thereof at random, freely, optionally or irregularly without forming any array wherein the carrier particles are arranged at positions or in order having a relationship corresponding to the various substances.

A seventh aspect of the invention is the carrier-enclosed transformable container wherein the carrier is a carrier which has plural predetermined different positions distinguishable from the outside, chemical substances being bonded or bondable to the positions, and which is formed into a linear, rod-like, planar or block form. Examples of the "block form" include spherical, cylindrical, cubic, rectangular parallelepiped, prismatic forms.

The carrier may be flexible or nonflexible. The carrier is enclosed into the carrier-enclosed transformable container by use of an enclosing portion. The enclosing portion may be formed by positioning the carrier to be contactable with a liquid sucked in the carrier-enclosed transformable container, and setting thereto a fitting tool for preventing the liquid from flowing out from the orifice part. Usually, a chemical substance which is bonded or bondable to the predetermined individual positions on the carrier is one of the plural chemical substances.

An eighth aspect of the invention is the carrier-enclosed transformable container wherein the non-transformable portion has a thick-tube portion which can store liquid therein, a thin-tube portion or thin-layer portion which is thinner than the thick-tube portion, and a transition portion connected to the thick-tube portion and the thin-tube portion or thin-layer portion and arranged between the thick-tube portion and the thin-tube portion or thin-layer portion, the orifice part is located to be connected to the thin-tube portion or thin-layer portion, and the carrier is enclosed in the thin-tube portion or the thin-layer portion.

When the carrier particles in this case are held onto a single line in the thin-tube portion or held into a single layer state in the thin-layer portion, an easier measurement can be made by scanning the carrier particles along the thin-tube portion or capturing the whole of the thin layer in a lump as a planar image. The carrier particles are in a single line form or single layer form; therefore, in connection with the diameter of the thin-tube portion or any cross section thereof perpendicular to the axial direction, or the thickness of the thin-layer portion or any cross section thereof in the normal line direction, the carrier particles cannot pass each other, or two or more of the particles cannot be arranged in the direction perpendicular to the axial direction. Alternatively, the thin-tube portion or the thin-layer portion needs to have a shape or size not permitting two or more of the carrier particles to be arranged along the normal line direction. In short, the thin-tube portion has an inside diameter or width and the length larger than the liquid of the carrier particles and smaller than the value two times the outside diameter of the particles, or the thin-layer portion has a thickness smaller than the value two times the outside diameter.

As a result, the individual carrier particles enclosed in the thin-tube portion or the thin-layer portion can be measured by scanning the particles along the line, or can be collectively measured. The outside diameter of the carrier particles is from, for example, about 0.1 to 3 mm, and the thin tube is caused to have an inside diameter of, for example, about 0.2 to 6 mm.

The thin-tube portion and the thick-tube portion may be in a curved line form besides in a straight line form. They may be, for example, in the form of a spiral convoluting along the cylinder around the axis through which the orifice part and the fitting opening are jointed with each other or in the form of a spiral convoluting helically in a plane, may be curved, or may have a U-shaped portion. About the thin-tube portion and the thick-tube portion, any cross section thereof in the direction perpendicular to the fluid-flowing direction may be in a circular form or a ring from; besides, any cross section of the inner wall may be, for example, rectangular. When the carrier particles to be held are spherical, the apexes of the rectangle function as grooves through which a fluid can pass. The thin-layer portion is not limited to any planar portion, and may be in a curved surface form. In the thin-tube portion in which the carrier is enclosed, the volume of the space which can contain a fluid is from, for example, about several microliters to several hundreds of microliters.

A ninth aspect of the invention is the carrier-enclosed transformable container which has an enclosing portion for enclosing the carrier in the containing part in the state that the carrier can contact a fluid flowing from the orifice part to the containing part.

An example of the enclosing portion is a portion having one or more carrier-passage-blocking members arranged as follows in such a manner that when the orifice part has a size permitting the carrier to pass through this part, a fluid can pass through the enclosing part but the carrier cannot pass therethrough: the members are arranged to be separated from the holding portion and further to partition the containing part oppositely to the flowing direction of the fluid.

The "carrier-passage-blocking member(s)" is/are (each) formed by a member separated from the carrier-enclosed transformable container. The carrier-passage-blocking member(s) may (each) be made of a combination of such a member with a portion obtained by working the wall of the carrier-enclosed transformable container or the like, the wall of the carrier-enclosed transformable container or the like. The carrier-passage-blocking member is combined with the inner wall of the container to form a gap, whereby a fluid can pass therein. The through hole or gap has a size or shape not permitting the carrier particles to pass through the hole or gap. The carrier-passage-blocking member is (each), for example, a member arranged to partition the thin tube into a wheel form, cross form, single-line form, radial form, net form or ring form, or a penetratable porous member having a through hole. In the case of the penetratable porous member, various carrier particles having a size larger than the pore diameter can be certainly enclosed. The "penetratable porous member" does not need to be a filter for capturing some substance by adsorption or the like. However, in a case where the enclosing portion is a thinly membranous filter such as a filter or a membrane, the filter can not only prevent the outflow of the carrier from the orifice part but also capture a predetermined substance. In a case where the enclosing portion is arranged separately from the carrier-enclosed transformable container, the following is used: a member made into the form of a thin plate or thin membrane that is thin in the fluid-flowing direction, or a penetratable porous member having a large pore diameter under conditions that the carrier does not flow out. About the number of the carrier-passage-blocking member(s), it is preferred that at least one of the carrier particles is located on the orifice part side in order to prevent the carrier particles from flowing out from the orifice part.

When the separately arranged carrier-passage-blocking member(s) is/are set to be freely attached or removed, the carrier can easily be enclosed and pulled out.

When the enclosing portion is set by working the carrier-enclosed transformable container so as to be narrowed, the pressure necessary for the suction and the discharge can be decreased by making the opening portion large under conditions that the carrier does not flow out. Examples of the enclosing portion made by use of the carrier-enclosed transformable container itself include an enclosing portion wherein a project portion is located to be projected in the central direction of the thin tube in order to make the thin tube so as to be narrowed; an enclosing portion having one or more projected regions obtained by projecting the wall face of the holding portion so as to partition the holding portion oppositely to the fluid-flowing direction; and an enclosing portion using a stopper in a short-tube form.

In this way, the carrier particles can be certainly enclosed, without working the carrier particles, by working or deforming the carrier-enclosed transformable container.

A tenth aspect of the invention is the carrier-enclosed transformable container wherein the enclosing portion has an introducing hole made in the wall face of the containing part so as to permit the carrier to be introduced into the containing part, and a cover for covering the introducing hole.

In this case, the size of the introducing hole is preferably made larger than the size of the orifice part. This makes it possible to enclose the carrier which cannot pass through the orifice part into the containing part.

An eleventh aspect of the invention is the carrier-enclosed transformable container wherein a region into which the carrier is enclosed, in the non-transformable portion, is set to be freely attached and removed.

This aspect makes it possible to enclose the carrier easily by attaching this portion to the body of the carrier-enclosed transformable container.

A twelfth aspect of the invention is the carrier-enclosed transformable container wherein a bellows is formed in the transformable wall face. The "bellows" is a face-form member or membrane-form member having waves or pleats having mountains and valleys formed along a direction that traverses the predetermined transformable direction substantially perpendicularly thereto, the bellows being permitted to be folded down at the mountains and the valleys. In the case of using the face-form member or membrane-form member wherein a bellows is formed in a wall face surrounding the axis in the transformable direction cylindrically, the shape of the waves or the pleats is made of mountains or valleys in the form of a straight line perpendicular to the transformable direction, or in the form of a circumference or a closed curved line (which may be a straight line) contained in a plane perpendicular to the transformable direction.

For example, the bellows is formed to partition the entire wall face of the containing part to two in a direction which traverses the transformable direction of the bellows. Accordingly, the transformable direction is substantially consistent with the normal line direction of a plane containing each of the mountains or valleys of the waveform or the pleats of the bellows.

A thirteen aspect of the invention is a carrier-enclosed transformable container processing apparatus having: one or more carrier-enclosed transformable containers (each) having a containing part which can contain liquid and gas at its inside surrounded by a wall face, a part of this wall face having a transformable wall face capable of undergoing a predetermined transformation without changing the entire internal surface area of the wall face substantially, an orifice part which is connected to the containing part and can undergo the inflow and outflow of a liquid sucked and discharged by the expansion and contraction of the inside by the transformation of the transformable wall face, respectively, and a carrier to which a predetermined substance enclosed in the containing part to be in a substantially stationary state is bonded or bondable; and one or more carrier enclosed heads for supporting the carrier-enclosed transformable container(s) in the manner that the orifice part is not changed or moved by the transformation of the transformable wall face, and causing the transformable wall face of the carrier-enclosed transformable container(s) to be transformed, thereby sucking a liquid into the carrier-enclosed transformable container(s) and discharging the liquid therefrom.

The wording "supporting the carrier-enclosed transformable container(s) in the manner that the orifice part is not changed or moved by the transformation of the transformable wall face" means that (each of) the carrier-enclosed transformable container(s) is attached to the head in the manner that the position and the shape of the orifice part are not substantially changed or moved by the transformation of the transformable wall face. This is based on the following reason: in this carrier-enclosed transformable container, it is unnecessary that a plunger and an orifice part which slide when a liquid is sucked or discharged are formed as members independently of each other, as carried out in a cylinder-type partitioning chip, but the transformable wall face and the orifice part, which are transformed when a liquid is sucked or discharged, are formed as members continuous to each other. For example, the position where the carrier-enclosed transformable container is fitted or fixed to the head, or is supported on the head in any other manner is the non-transformable wall face, which is not transformable, other than the transformable wall face located between the orifice part and the transformable wall face. The orifice part is preferably supported downwards.

A fourteenth aspect of the invention is the carrier-enclosed transformable container processing apparatus which further has a holder group having plural holders in which various liquids such as various solutions or suspensions can be held, and a head moving unit for moving (each of) the carrier enclosed head(s) relatively to the holder group, wherein the individual holders set in the holder group are located in the manner that the orifice parts can be simultaneously inserted.

A fifteenth aspect of the invention is the carrier-enclosed transformable container processing apparatus wherein the holders are wells, the holder group is at least one micro plate wherein the wells are arranged in a matrix form, the carrier-enclosed transformable containers of the carrier enclosed head(s) are arranged in a matrix form, all the orifice parts set to the carrier enclosed head are located in the manner that the orifice parts can be simultaneously inserted in the whole or a part of the wells in the micro plate, at least one of the row interval or the column interval of the orifice parts is set to a natural number multiple of the row interval or the column interval of the corresponding wells, respectively, and at least one of the row number or the column number of all the corresponding orifice parts is one-to-the-natural-number of the row number or the column number of the wells.

The "matrix form" means a structure wherein elements, such as the wells or the orifice parts of the carrier-enclosed transformable containers, are arranged along two directions of a column direction and a row direction at a predetermined row interval and a predetermined column interval, the row number and the column number of the elements being each predetermined. The row number and the column number are each 2 or more. The column direction and the row direction are usually orthogonal to each other; however, the directions are not necessarily thereto. Thus, the directions may be obliquely intersected. The matrix form also includes a case in which in individual rows or columns adjacent to each other, for example, the row or columns are shifted from each other by a length of a half of the column interval or the row interval so that the elements are alternated with each other, thereby arranging the elements into a closed-pack form. The "row interval" means the distance in the column direction between in a row wherein any one out of elements arranged in a matrix form is located and a row wherein an element adjacent to the element in the column direction is located. The "column interval" means the distance in the row direction between a column wherein any one out of elements arranged in a matrix form is located and a column wherein an element adjacent to the element in the row direction is located.

Since "all the orifice parts are located in the manner that the orifice parts can be simultaneously inserted in the whole or a part of the wells in the micro plate", the row number or the column number of the matrix of the orifice parts is generally smaller than that of the matrix of the wells. It is necessary that the matrix of the orifice parts is equal to that of the wells in the angle made between the row direction thereof and the column direction thereof, and the row interval or the column interval of the matrix of the orifice parts is a natural number multiple of the row interval or the column interval of the matrix of the wells.

Since "at least one of the row interval or the column interval of the orifice parts is set to a natural number multiple of the row interval or the column interval of the corresponding wells, the natural number being 2 or more, respectively, and at least one of the row number or the column number of the corresponding orifice parts is one-to-the-natural-number of the row number or the column number of the wells", the following are present: matrix-form well arrangements which each have the same configuration as the matrix arrangement of the orifice parts, and do not overlap with each other, the number of the well arrangements being at least a natural number (>1) (the well arrangements being referred to as "partial well matrixes" hereinafter). Besides, any one of the well-elements belonging to any one of the partial well matrixes and the corresponding one well-element belonging to the partial well matrix(es) adjacent to the matrix are not apart from each other by a length not less than the distance between adjacent ones of the wells in the micro plate.

Thus, although independent well groups, which of each all the orifice parts of the carrier enclosed head can be simultaneously inserted into, are present in a number of 2 or more, the area for working can be restricted to the inside of the micro plate alone, which has an area consistent with that of the carrier enclosed head; therefore, the working area does not become large in vain. About the movement of the carrier enclosed head between the partial well matrixes, all the orifice parts of the carrier enclosed head can be positioned to be permitted to be inserted into all the partial well matrixes in the micro plate by repeating a movement corresponding to at longest the distance of the row interval or the column interval at least (N–1) times wherein N is a natural number (>1).

Since the natural number is 2 or more, it is necessary that at least either one of the row number or the column number of the wells in the micro plate is a number having this natural number (>1) as a divisor thereof. About, for example, a carrier enclosed head having orifice parts arranged to have a column interval 3 times larger than that of a micro plate having wells arranged in the form of a matrix of 4 rows×12 columns, the natural number corresponds to "3". The column number of the orifice parts is 4, which is 1/"3" of 12, which is the column number of the wells. In such a way, twelve, which is the column number of the wells, has "3" as a divisor thereof.

A sixteenth aspect of the invention is the carrier-enclosed transformable container processing apparatus which further has a control unit, wherein the control unit causes the above-mentioned carrier enclosed head to cause all the orifice parts to be positioned in such a manner that the orifice parts can be simultaneously inserted into the wells belonging to a first partial well matrix, which is the corresponding partial well matrix, in the micro plate, and then causes the moving means to attain a relative movement between the carrier enclosed head and the micro plate, thereby causing all the orifice parts to be positioned in such a manner that the orifice parts can be simultaneously inserted into the wells belonging to a second partial well matrix, which is the corresponding partial well matrix, in the micro plate.

The reason why the above has described only a case where the apparatus has the "first partial well matrix" and the "second partial well matrix" is that the number of the partial well matrixes is at least the natural number (>n). In a case where the wells in the micro plate have an ordinary matrix-form configuration, all the orifice parts can be simultaneously inserted into all the partial well matrixes in the micro plate by carrying out a relative movement between the carrier enclosed head and the micro plate at least the natural number (>n) along the corresponding column direction and/or row direction by the distance of the row interval or column interval of the wells in the micro plate.

In a case where the row interval and the column interval of the orifice parts are a natural number (n>1) multiple of the row interval of the wells and a natural number (m>1) multiple of the column interval of the wells, respectively, the number of the partial well matrixes is nm in total for the micro plate alone.

A seventeenth aspect of the invention is the carrier-enclosed transformable container processing apparatus wherein the individual partial well matrixes along a moving path of the carrier enclosed head hold liquids, such as solutions or suspensions, necessary for individual steps of the processing in accordance with the order of the steps.

The "moving path" is a path through which the carrier enclosed head passes when the carrier enclosed head is moved in parallel successively over all the partial well matrixes, and is preferably a path the distance of which is the shortest along the moving course. Accordingly, selection from the individual partial well matrixes is made in accordance with the order of the treating steps, and then the necessary solutions, such as reagents, and others are held therein. For example, solutions or suspensions to be handled so as to be equivalent to each other in kind or amount are held in the wells belonging to the same one (i.e., single one) out of the partial well matrixes, and solutions or suspensions to be handled so as to be different from each other in kind or amount are held in between the wells belonging to any different ones out of the partial well matrixes. This is because sucking or discharging operations of the individual carrier-enclosed transformable containers fitted to the same carrier enclosed head are linked to each other so that the individual operations are substantially identical. Alternatively, in the case of handling a liquid in a great volume, solutions or suspensions of the same kind may be held even in the wells belonging to different ones out of the partial well matrixes.

An eighteenth aspect of the invention is the carrier-enclosed transformable container processing apparatus wherein the control unit causes (each of) the carrier enclosed head(s) to be successively moved so as to position the same orifice part out of the orifice parts, which are fitted to the carrier enclosed head, in the state that the same orifice part can be inserted into all the wells belonging to each of well groups in the micro plate, the same orifice part being permitted to be inserted into each of the well groups.

Each of the well groups contains one of the well elements belonging to each of the partial well matrixes without overlapping two or more thereof. Accordingly, the element number of the wells belonging to each of the well groups is equal to the number of the partial well matrixes present in the micro plate alone. In other words, according to this manner, the orifice parts of the individual carrier-enclosed transformable containers are in the state that the orifice parts can be simultaneously inserted into the respective corresponding wells in all the well groups. The number of the wells belonging to each of the well groups is at least the above-mentioned natural number (n>1). When the row interval and the column interval of the orifice parts of the carrier-enclosed transformable containers are natural number multiples (n>1, and m>1) of the row interval and the column interval of the wells, respectively, the number of the wells belonging to each of the well groups is nm. The moving path of each of the orifice parts inside each of the well groups is a path permitting the orifice part to pass through all the well elements in the well group in accordance with the order of the treating steps, and is preferably a path the distance of which is the shortest.

It is preferred that partitions for partitioning the well groups, in the micro plate, into each of which the same orifice part out of the orifice parts fitted to the carrier enclosed head can be inserted, from each other are built on the upper surface of the micro plate so as to be projected therefrom.

According to this manner, for example, a large number of different specimens to be treated can be treated in the state that the specimens are partitioned from each other with the partitions; therefore, once any one of the orifice parts is moved into one of areas surrounded by the partitions, the processing can be conducted without moving the orifice part over any one of the partitions.

The number of the above-mentioned carrier enclosed head(s) and the number of the micro plate and other equivalent optional micro plates are each at least the natural number. At this time, the individual carrier enclosed heads can be set up or controlled to cause the operations of the heads to be linked with each other.

A nineteenth aspect of the invention is the carrier-enclosed transformable container processing apparatus wherein (each of) the carrier enclosed head(s) is provided with a magnetic force means having two or more magnets set to the containing parts so as to be brought into contact with and separated from the containing parts in the manner that a magnetic field can be simultaneously applied to the containing parts and can further be removed. Usually, a case where the magnetic field is applied is a case where magnetic particles as the carrier are contained in the carrier-enclosed transformable containers or a case where instead of the carrier-enclosed transformable containers, partitioning chips are fitted to the carrier enclosed head(s).

The magnetic force means has, for example, comb-tooth members that are arranged between orifice part rows or orifice part columns having a row interval or column interval set to a natural number multiple of the row interval or the column interval of the wells arranged in the matrix form, the natural number being two or more, so as to be permitted to be relatively moved in the row direction or the column direction, that extend along the row direction or the column direction, and further that are each formed to have a width permitted to be inserted in between the orifice part rows or the orifice part columns, the number of the comb-tooth members being, for example, (the row number of the carrier-enclosed transformable containers −1) or (the column number thereof −1); and a supporting member connected to single-ends of the comb-tooth members. Each of the comb-tooth members is provided with magnets arranged at positions corresponding to the individual carrier-enclosed transformable containers, so as to have the above-mentioned column interval or row interval, the number of the magnets being equal to the number of the columns or that of the rows. When a magnetic field is applied to the carrier-enclosed transformable containers, all the magnets are moved to give the shortest distances from all of the individual carrier-enclosed transformable containers. When the magnetic field is removed or made weak, all the magnets are completely withdrawn from the head wherein the carrier-enclosed transformable containers are arranged. Alternatively, the individual magnets may be moved at intermediate positions having predetermined intervals from the carrier-enclosed transformable containers. The number of the comb-tooth members may be as described above; besides, when each of the magnets arranged in each of the comb-tooth members is set to have an effect on two, out of the carrier-enclosed transformable containers, arranged on both sides of the magnet, it is sufficient that the number of the comb-tooth members is approximately half the above-mentioned number.

A twentieth aspect of the invention is the carrier-enclosed transformable container processing apparatus wherein (each of) the carrier enclosed head(s) further has a photodetector for detecting the state of the containing part(s) Accordingly, at least the non-transformable portion of the carrier-enclosed transformable container(s) needs to be made of a translucent member. The "state of liquid" may be whether or not the liquid is present, or may be the sucking volume of the liquid, or the discharging volume of the liquid.

The photodetector is, for example, a photodetector having comb-tooth members that are arranged between orifice part rows or orifice part columns of the carrier-enclosed transformable container having a row interval or column interval set to a natural number multiple of the row interval or the column interval of the wells, the natural number being two or more, so as to be permitted to be relatively moved in the row direction or the column direction, that extend along the row direction or the column direction, and further that are each formed to have a width permitted to be inserted in between the orifice part rows or the orifice part columns, the number of the comb-tooth members being, for example, (the row number of the orifice parts −1) or (the column number thereof −1); and a supporting member connected to single-ends of the comb-tooth members. Each of the comb-tooth members is provided with a photo-detecting unit.

A twenty-first aspect of the invention is the carrier-enclosed transformable container processing apparatus wherein the photodetector has one or more light-receiving terminals arranged outside the non-transformable portion of the containing part(s) and near the non-transformable portion to surround the non-transformable portion, or one or more light-receiving terminals and at least one radiating terminal arranged in the same manner as described above, and the photodetector can be moved relatively to the non-transformable portion so as to scan the whole of a region where the carrier particles can be contained, the region being in the non-transformable portion.

Since the "photodetector can be moved relatively to the non-transformable portion", the following cases are caused: a case where the non-transformable portion is moved; a case where the photodetector is moved; and a case where the two are moved.

A twenty-second aspect of the invention is the carrier-enclosed transformable container processing apparatus wherein (each of) the carrier enclosed head(s) causes the transformable wall face to be transformed at intersections between the transformable wall face and a straight line passing through the insides of the orifice part and the containing part to penetrate the transformable wall face, and along the straight line.

A twenty-third aspect of the invention is the carrier-enclosed transformable container processing apparatus wherein (each of) the carrier enclosed head(s) has a carrier-containing-part-supporting portion capable of supporting the two or more carrier-enclosed transformable containers, and a movable member that can simultaneously advance and retreat along a predetermined transformable direction of the transformable wall faces of the carrier-enclosed transformable containers.

A twenty-forth aspect of the invention is the carrier-enclosed transformable container processing apparatus which has a control unit for controlling the transformation of the transformable wall, and/or movement between the carrier enclosed head(s) and the holder groups on the basis of: the number or the structure of the carrier-enclosed transformable container(s); a liquid to be sucked and discharged, a substance contained therein, the amount thereof, the containing position thereof, the temperature thereof or the concentration thereof; the content of a processing; or instructions.

A twenty-fifth aspect of the invention is the carrier-enclosed transformable container processing apparatus wherein about the transformation of the transformable wall face, a predetermined standard position is set, and the transformation of the transformable wall face is controlled with reference to the standard position.

The "predetermined standard position" is decided in accordance with the volume of the liquid handled in a processing, the volume of the used carrier-enclosed transformable container(s), the content of the processing, the work precision of the carrier-enclosed transformable container(s), or the like. The standard position is rendered a position along the transformable direction of the movable member or the transformable wall face in the state that a predetermined transformation is already applied to the carrier-enclosed transformable container(s) when the volume of the liquid handled in a processing is minute (for example, a volume in an order from several microliters to several hundreds of microliters), the volume of the used carrier-enclosed transformable container(s) is small, precision is required for the processing, or the work precision of the carrier-enclosed transformable container(s) is not high. This makes it possible to make a highly precise control. In this case, for example, it is preferred to set the apparatus to make it possible to discharge all of a predetermined maximum suction volume of a liquid into the carrier-enclosed transformable container(s) on the basis of a predetermined maximum transformable amount. This makes it possible to prevent the liquid from remaining in the carrier-enclosed transformable container(s) through the discharge of the liquid from the carrier-enclosed transformable container(s).

In the case of representing a predetermined volume of the inside of (each) of the carrier-enclosed transformable container(s) by $V_0$, and representing a predetermined maximum internal volume of the carrier-enclosed transformable container by a transformation thereof and a predetermined minimum internal volume of the container by a transformation thereof by $V_1$ and $V_2$, respectively, provided that the position of the movable member or the transformable wall face corresponding to the state that the volume of the container is $V_0$ is used as a standard or reference, it is preferred to set the standard position in such a manner that the predetermined maximum suction volume $V_1-V_0$ of a liquid in the carrier-enclosed transformable container is smaller than the predetermined maximum discharge volume $V_0-V_2$ thereof, that is, the relationship of $V_1-V_0 \leq V_0-V_2$, that is, $(V_1+V_2)/2 \leq V_0$ is satisfied.

Since the attained transformation is a "predetermined maximum transformation", the transformation is not necessarily a physically maximum transformation. Since "all of the maximum suction volume can be discharged", it is necessary that the "maximum discharge volume" is equal to or more than the "maximum suction volume". This makes it possible to conduct any processing without taking care of the remaining volume of the liquid in the carrier-enclosed transformable container(s).

On the other hand, when the volume of the handled liquid is large (for example, a volume in an order of several milliliters), or precision is not required very much for a processing, a control may be made using, as a standard or reference, a position of the movable member in a non-transformed state that the carrier-enclosed transformable container(s) is/are not transformed. Such a case is, for example, a case where in the state that the movable member is not yet brought into contact with the carrier-enclosed transformable container(s) and further a position along the transformable direction (for example, a position apart from the chip(s) by 1 mm) is used as the standard position.

A twenty-sixth aspect of the invention is the carrier-enclosed transformable container processing apparatus wherein the orifice part is located at a lower end thereof, the containing part is located over the orifice part, a part of the wall face surrounding the containing part has the transformable wall face transformable in the vertical direction so as to partition the inner wall face into upper and lower regions, the upper end of the containing part and the movable member are set to be brought into contact with each other or connected to each other.

A twenty-seventh aspect of the invention is the carrier-enclosed transformable container processing apparatus wherein the containing part has a transformable portion that contacts or can contact the movable member, has a transformable wall face transformable by the movable member, and can contain gas; and a non-transformable portion that is connected to the transformable portion, is made of a non-transformable wall face, which is not transformable, has the orifice part at its tip, and can store liquid.

A twenty-eighth aspect of the invention is a carrier-enclosed transformable container processing method, having a supporting step of supporting, onto a carrier enclosed head, two or more carrier-enclosed transformable containers each having a containing part which can contain liquid and gas at its inside surrounded by a wall face, a part of this wall face having a transformable wall face capable of undergoing a predetermined transformation without changing the entire internal surface area of the wall face substantially, an orifice part which is connected to the containing part and can undergo the inflow and outflow of a liquid sucked and discharged by the expansion and contraction of the inside by the transformation of the transformable wall face, respectively, and a predetermined carrier, to which a predetermined substance enclosed in the containing part is bonded or bondable, in the manner that the orifice parts are not changed or moved by the transformation of the transformable wall face; a moving step of moving the carrier enclosed head; and a transforming step of inserting the orifice parts into holders of a holder group, and transforming the transformable walls simultaneously.

A twenty-ninth aspect of the invention is the carrier-enclosed transformable container processing method, wherein the transforming step is the step of setting a predetermined standard position about the transformation of the transformable wall face, and transforming the transformable wall face, using the standard position as a standard or reference.

A thirtieth aspect of the invention is the carrier-enclosed transformable container processing method, wherein the orifice part is located at a lower end thereof, the transformable wall face is located at a part of the wall face surrounding the containing part so as to be transformable in the vertical direction, and the containing part has a transformable portion which is located over the orifice part, has the transformable wall face, and can contain gas, and a non-transformable portion which is connected to the transformable portion, has none of the transformable wall face, has the orifice part, and can store liquid, and the transforming step has the step of bringing a movable member into contact with the upper end face of the containing part or connecting the movable member thereto, and the step of lowering and/or raising the movable member.

A thirty-first aspect of the invention is the carrier-enclosed transformable container processing method, wherein the movable member is raised and lowered by setting a predetermined standard position along the vertical direction in which the transformable wall face is transformed, and using the standard position as a standard or reference.

A thirty-second aspect of the invention is the carrier-enclosed transformable container processing method, wherein a magnetic body to which a predetermined substance is bondable or bonded is suspended in the liquid, the method having the step of applying a magnetic field to the inside of the containing part or the holders of the holder group, thereby causing the magnetic body to be adsorbed on the inner wall of the containing part or the holders so as to separate the magnetic body.

A thirty-third aspect of the invention is a carrier-enclosed transformable container processing method, having: a first step of preparing a micro plate in which wells are arranged in a matrix form, and one or more carrier enclosed heads (each) having orifice parts of carrier-enclosed transformable containers that are capable of sucking and discharging a fluid and are arranged in a matrix form, at least one of the row interval or the column interval of the orifice parts being set to a natural number multiple of the row interval or the column interval of the wells, the number of the natural number being 2 or more, and at least one of the row number or the column number of the corresponding orifice parts being one-to-the-natural-number of the row number or the column number of the wells, and then moving (each of) the carrier enclosed head(s) relatively to the micro plate, thereby positioning all the orifice parts set to the carrier enclosed head to be permitted to be simultaneously inserted into the wells belonging to a first partial well matrix in the micro plate; and a second step of attaining a relative movement between the carrier enclosed head and the micro plate, thereby positioning all the orifice parts to be permitted to be simultaneously inserted into the wells belonging to a second partial well matrix, which is the corresponding partial well matrix, in the micro plate.

The reason why a case where the method has only the "first step" and the "second step" has been described herein is that the number of partial well matrixes is at least the natural number (n>1). Accordingly, in a case where the row interval and the column interval of the orifice parts are a natural number (n>1) multiple of the row interval of the wells and a natural number (m>1) multiple of the column interval of the wells, respectively, the number of the partial well matrixes is nm in total for the micro plate alone. Thus, the number of steps is nm in total for the micro plate alone.

In a case where the matrix-form arrangement is an ordinary matrix-form arrangement, all the orifice parts can be simultaneously inserted into all the well matrixes in the micro plate by repeating a relative movement between the carrier enclosed head and the micro plate, the distance of the movement being equal to the row interval or the column interval of the wells in the micro plate, at least natural number (n>1) times along the corresponding column direction or row direction.

In order to conduct a treatment in the first step, this step is caused to have the step of inserting the orifice parts into the individual wells to perform suction or discharge, and the step of pulling out the orifice parts from the wells. The second step is also caused to have the same inserting step, sucking and discharging step or pulling-out step as in the first step. The number of necessary steps is decided at least in accordance with the natural number (n>1), and is at least the natural number.

ADVANTAGEOUS EFFECTS OF THE INVENTION

According to the first, thirteenth and twenty-eighth aspects of the invention, the carrier, to which various substances such as biogenic substances, are bonded or bondable, is enclosed into the transformable container, which is transformable, to be in a stationary state, and then the transformable container is mechanically transformed, whereby a liquid can be sucked and discharged. Accordingly, the suction of a fluid into the transformable container, the contact between the fluid and the carrier, and the discharge of the fluid can be attained without using any complicated fluid mechanical mechanism, such as a channel for causing liquid or gas to flow, for example, a cylinder. Furthermore, the apparatus can be produced at low costs, and the method can easily be conducted manually or by use of the apparatus, which is easy to handle and has a simple structure.

By transforming the transformable wall face without changing the entire internal surface area of the wall face, treatments of liquid, such as suction and discharge thereof, are conducted; therefore, complete watertightness and airtightness are gained and a highly reliable processing can be conducted without requiring members which constitute the wall face to be fitted into each other or be slid on each other, nor requiring a high working precision.

Various treatments can be conducted only by sucking and discharging liquid and moving the carrier-enclosed transformable container while the carrier, to which a predetermined substance is bonded or bondable, is enclosed in the containing part having the orifice part, examples of the treatments including reaction, washing, temperature-control, separation, agitation, partition, clarification, isolation, elution, and extraction. Thus, an effective and speedy processing can easily be attained.

Furthermore, according to the invention, treatments of from reaction with the predetermined substance bonded to the carrier to measurement of the substance can be conducted in the state that the substance is enclosed in the carrier-enclosed transformable container, only the orifice part of which is open. Thus, a target processing can be conducted to the last without bringing the predetermined substance into contact with any other member or hand. As a result, cross-contamination is prevented so that the processing can be reliably and surely attained. When the carrier-enclosed transformable container is selected to have a shape suitable for the speed of fluids or liquid volumes to be handled, the apparatus can be caused to cope with various treatments. Thus, the invention is versatile and variable.

Additionally, according to the invention, the carrier is held in a substantially stationary state but is not moved by applying fluid force thereto. Thus, the handling and measurement of the carrier can be made easy by a simple control without making any complicated synchronous control or the like.

According to the second aspect of the invention, the carrier is surrounded by the non-transformable wall face; therefore, a bad effect is not produced onto the carrier by the transformation. Additionally, a measurement can be stably made from the outside, so it is high in reliability.

According to the third aspect of the invention, liquids having at least two different volumes can be certainly sucked into the containing part and certainly discharged therefrom by selecting appropriate one or ones from the transformable portions without adjusting the magnitude of force applied to the transformable portions. In particular, about both of a small amount of liquid and a large amount of liquid, respectively, a predetermined volume thereof can be certainly sucked and discharged by hand, respectively. Thus, the aspect is high in reliability.

According to the fourth aspect of the invention, usually, the carrier-enclosed transformable container is used in the state that the orifice part is faced downwards and the container is fixed to be supported from the lower side; therefore, when the container is transformed along the vertical direction, the change and movement of the orifice part by the transformation can be certainly prevented.

According to the fifth aspect of the invention, about the carrier particles or the carrier particle groups, the carrier particles, which are not exchanged, are used to the last to conduct the fixation, reaction and measurement of various substances, and other operations. Thus, the aspect is suitable for a series of treatments conducted automatically to the last.

According to the sixth aspect of the invention, various substances held on the carrier particles are not distinguished on the basis of positions caused to correspond to the carrier particles. It is therefore unnecessary that while the individual carrier particles are strictly fixed to individual positions or while the order thereof is strictly kept, the carrier particles are strictly measured. Moreover, the particles are not moved by applying fluid force thereto, but the particles are kept in a substantially stationary state; therefore, the handling and measurement of the individual carrier particles can be made easy and the measurements can be made highly precise by a simple control without making a complicated synchronous control or the like.

According to the invention, the carrier particles to which various substances are bonded or bondable can easily be introduced to the containing part for holding the particles, or held therein without deciding the positions or order thereof beforehand. Accordingly, treatments of the carrier particles themselves, such as a fixing treatment thereof, can easily be conducted in a place different from the containing part; thus, the efficiency, the reliability and the certainty of the processing can be made high.

According to the invention, in the case of marking the carrier particles to which various substances are bonded or bondable before the particles are held, holding the carrier particles in a substantially stationary state at any positions and then measuring the substances, a sufficient result is obtained if it is measured whether or not the marked substances are present. Thus, minute positional coordinates do not need to be measured. As a result, the measurement is easy.

Furthermore, according to the invention, the carrier particle groups, which each have plural carrier particles, can be marked in accordance with the individual groups. Accordingly, out of the carrier particles belonging to each of the groups, carrier particles to which various substances are fixed or fixable are made different from carrier particles used for the marking, whereby the carrier particles can be caused to have different functions in accordance with the individual particles. Thus, the carrier particles can be caused to have specialized functions, such as marking and fixing functions, in accordance with the individual particles. As a result, a more precise processing can be performed.

Moreover, by setting, at will, the number of the carrier particles belonging to each of the carrier particle groups, various markings can be attained; thus, the invention is expandable, variable, and versatile.

According to the seventh aspect of the invention, the plural chemical substances are bonded or bondable to plural positions of an individual of the carrier. Thus, by arranging the positions, to which the chemical substances are bonded or bondable, regularly, for example, at constant regular intervals or in a specified direction, the chemical substances at the individual positions can be easily and certainly specified.

According to the eighth aspect of the invention, the carrier is enclosed in the thin-tube portion or the thin-layer portion; thus, when the carrier particles are held in the thin-tube portion or the thin-layer portion to be arranged, for example, in a single line or in a single layer state, the individual carrier particles are one-dimensionally or two-dimensionally held, whereby a certain measurement can be made. When the carrier particles are scanned along the thin-tube portion or the thin-layer portion to make a measurement, the measurement can be made easy.

Furthermore, when a fluid is introduced or discharged along the thin-tube portion, contact between the fluid and the carrier can be certainly attained. Moreover, the thin-tube portion can be introduced into various holders set in the outside. This is convenient for sucking and discharging liquid. Additionally, according to the invention, the carrier particles and the fluid can be treated in the state that they can contact each other at any time; thus, the efficiency of the treatment is high.

According to the ninth aspect of the invention, the enclosing portion is set, the portion being a portion for enclosing the carrier from the orifice part into the containing part in the state that a fluid which flows into the containing part can contact the carrier, thereby making it possible to attain the enclosing of the carrier by use of the enclosing portion after the container is produced, which is different from a case where a container is produced in the state that the carrier is beforehand enclosed in the container. Thus, the container can easily be produced.

According to the tenth aspect of the invention, the carrier can be introduced through the introducing hole made in the containing part, and then air-tightly confined with the cover. It is therefore unnecessary that the carrier is introduced from the orifice part. Thus, by making the orifice part to have a size not permitting the carrier to pass through this part, the carrier can be certainly enclosed. Moreover, the carrier can be removed from the introducing hole.

According to the eleventh aspect of the invention, the region into which the carrier is enclosed, in the non-transformable portion, is set to be freely attached and removed, whereby the introduction of the carrier into the containing part can be made easy. In the case of preparing such plural regions beforehand, an effective processing can be conducted.

The twelfth aspect of the invention is an aspect wherein a bellows is formed in the transformable wall face. This makes it possible to form a wall face having a large transformation ratio through simple structure. Moreover, the wall face can be formed by a rigid member. Thus, the wall face is not broken. Furthermore, when the wall face is transformed, folded-down positions thereof or the direction in which the wall face is folded down is decided; thus, the regularity of the transformation or the shape resulting from the transformation is highly fixed.

According to the fourteenth aspect of the invention, by use of only the mechanical mechanism which neither contacts any gas nor any liquid to be moved along the transformable direction, the gas or liquid being a treatment target, treatments of a liquid, such as suction, discharge and transfer thereof, are made possible. Thus, the region which can contact the liquid is limited substantially to the closed space in the carrier-enclosed transformable containers, and the holders. As a result, contamination can be certainly prevented.

Furthermore, each of the carrier-enclosed transformable containers is supported in such a manner that its orifice part is not changed or moved by force applied to transform the transformable wall face; therefore, a precise position control can be made by use of the carrier-enclosed transformable container. Thus, when a great number of such containers are arranged closely to each other, a speedy and effective processing can be conducted.

According to the fifteenth aspect of the invention, the carrier-enclosed transformable containers are supported in such a manner that their orifice parts are not changed or moved by force applied to transform the transformable wall face, and further the carrier-enclosed transformable containers can be simultaneously transformed under the same condition; therefore, a precise position control or a suction/discharge control giving a high reproducibility can be made. Even when the carrier-enclosed transformable containers are used, a large number of treatments can be conducted in parallel. Thus, an effective processing is attained. Even when the holders in a large number are arranged closely to each other, a highly reliable processing can be conducted.

At least one of the row interval or the column interval of the orifice parts is set to a natural number multiple of the row interval or the column interval of the corresponding wells, the natural number being 2 or more; therefore, two or more of the wells can be assigned to any one of the orifice parts. Accordingly, two or more solution species or the like can be incorporated in the micro plate alone without setting any new micro plate. Thus, a larger number of solution species or the like can be handled without increasing any working area.

Since two or more of the wells can be assigned to any one of the orifice parts, the single orifice part can handle a liquid having a volume two times or more the volume which any one of the wells handles. Furthermore, a large usable space makes its appearance between any adjacent ones of the orifice parts. The following can be set to each of the orifice parts without enlarging the scale of the apparatus: a mechanism for giving various functions, for example, a function of applying magnetic force to the orifice part, or a function of detecting the state of the liquid in the orifice part.

According to the sixteenth aspect or thirty-third aspect of the invention, the advantageous effects of the thirteenth and fourteenth aspects of the invention are produced; besides, the wells which (each of) the head(s) alone can handle at a time are each of the partial well matrixes which do not overlap with each other and belong to the micro plate alone, and further the individual partial well matrixes are separated from each other only by a distance corresponding to the distance between any adjacent ones of the wells in the micro plate. Therefore, when solutions or the like which are each necessary for a single treatment are incorporated into the partial well matrixes, respectively, the moving distance of the carrier-enclosed transformable container arrangement head up to the completion of the single treatment is permitted to be short. Thus, a speedy and effective processing can be conducted.

According to the seventeenth aspect of the invention, about the micro plate alone, a series of treatments made of plural steps for many targets to be treated can be continuously conducted to the last by use of the head alone. Thus, the treatment efficiency for the working area is high. Moreover, the moving distance of the head is permitted to be short; thus, the working efficiency is high.

According to the eighteenth aspect of the invention, each of the well groups contains one of the well elements belonging to each of the partial well matrixes without overlapping two or more thereof. Accordingly, by moving the orifice parts in such a manner that the parts are permitted to be inserted to all the wells belonging to each of the well groups, the following can be attained about the micro plate alone: a series of treatments made of steps the number of which is at least the natural number (n>1) can be continuously conducted, for many targets, in the micro plate alone to the last by use of (each of) the head(s) alone. The apparatus is high in reliability, and is easily managed.

According to the nineteenth aspect or thirty-second aspect of the invention, a magnetic field is applied to the insides of the containing parts or removed therefrom; thus, by causing magnetic particles in a liquid wherein the magnetic particles are suspended to be adsorbed to the insides, the particles can be certainly separated. Moreover, magnets having an intense magnetic force can be set up by use of gaps between any adjacent ones of the orifice part rows or orifice part columns, the gaps having an interval equal to the row interval or column interval of the orifice parts disposed in the head, the row interval or column interval being set to a natural number (2 or more) multiple of the row interval or column interval of the liquid wells. Accordingly, even when the micro plate is a micro plate wherein wells are densely integrated with each other, an intense magnetic field can be applied to the individual carrier-enclosed transformable containers and removed therefrom through simple mechanism.

According to the twentieth aspect of the invention, the state that a liquid is sucked or discharged is measured by detecting the state of the vicinity of the containing part of (each of) the carrier-enclosed transformable container(s) while surrounding the circumferential of the non-transformable portion of the containing part. Thus, a highly reliable control can be made.

According to the twenty-first aspect of the invention, one or more light-receiving terminals and/or one or more radiating terminals are set near the non-transformable portion of the containing part(s) to surround the circumference of the non-transformable portion; therefore, light emitted from carrier particles can be certainly captured. Thus, the apparatus is high in reliability.

According to the twenty-second of the invention, (each of) the transformable container(s) is transformed to pass through the orifice part; therefore, a fluid passing in the orifice part can be certainly sucked and discharged.

According to the twenty-third aspect of the invention, treatments of a liquid, such as suction, discharge and transfer thereof, are made possible by use of only a mechanical mechanism which causes the movable member to be moved along the transformable direction and does not contact gas or the liquid to be treated. Accordingly, a region which can contact the gas or liquid is limited substantially only to closed spaces in the carrier-enclosed transformable containers and the holders. As a result, contamination can be certainly prevented.

According to the twenty-forth aspect of the invention, the transformation of the transformable wall face and/or the movement of the head(s) is/are controlled on the basis of the structure of the carrier-enclosed transformable container(s) and so on. Thus, suction and discharge can be certainly attained.

According to the twenty-fifth, twenty-sixth and twenty-ninth aspects of the invention, on the basis of a standard transformable state permitted to undergo both of the expansion and contraction of the inside by the transformable wall face, the transformation is controlled. Thus, the apparatus can immediately cope with the expansion and the contraction of the inside by the transformation, so that a speedy and effective processing can be attained. Moreover, when the standard transformable state is suitably set, it is possible to prevent a liquid from remaining in the carrier-enclosed transformable container(s) through the discharge of the liquid.

According to the twenty-sixth aspect or thirtieth aspect of the invention, a gas is contained in the transformable portion having the transformable wall face, and an introduced liquid is stored in the non-transformable portion having no transformable wall face. Accordingly, the introduced liquid is not affected by the transformation of the transformable wall face, so as to prevent a situation that the liquid adhere onto the transformable wall face to remain thereon. Thus, the apparatus is high in reliability in a case where a quantitative treatment is conducted or in other cases.

BEST MODE FOR CARRYING OUT THE INVENTION

The following will describe carrier-enclosed transformable containers, carrier-enclosed transformable container processing apparatuses, and processing methods thereof according to embodiments of the invention on the basis of drawings.

FIG. 1 are views illustrating a carrier-enclosed transformable container 11 according to a first embodiment of the invention. As illustrated in FIG. 1(a), the carrier-enclosed transformable container 11 has a containing part 12 which can contain liquid and gas at its inside surrounded by a wall face, a part of this wall face having a transformable wall face capable of undergoing a predetermined transformation without changing the entire internal surface area of the wall face substantially; an orifice part 13 which is connected to the containing part 12 and can undergo the inflow and outflow of a liquid sucked and discharged by the expansion and contraction of the inside by the transformation of the transformable wall face, respectively; and carrier particles 14 and 15 to which predetermined substances enclosed in the containing part 12 to be in a substantially stationary state are bonded or bondable. The containing part 12 has a single transformable portion 16 surrounded by the transformable wall face, and a non-transformable portion 17 connected to the transformable portion 16, surrounded by a non-transformable wall face, which is not transformable, and connected to the orifice part 13, the inside of the non-transformable portion 30 being permitted to be measured from the outside.

In the transformable portion 16, a bellows 18 is fitted to its transformable wall face. The bellows 18 is formed to partition the entire wall face of the containing part 12 or the transformable wall face of the transformable portion 16 into two in a direction which traverses the axial direction of the transformable portion 16 or the containing part 12, which is along the transformable direction. One of the partitions has an apex 19. The other has the non-transformable portion 17; and a flange 20 that is arranged in the boundary between the transformable portion 16 and the non-transformable portion 17, is used to support the carrier-enclosed transformable container 11 mainly by hand or between fingers and thumb, and has a larger radius than the transformable portion 16 and the non-transformable portion 17 each have, so as to be projected outwards. Accordingly, this carrier-enclosed transformable container 11 is suitable for manual operation. The normal line direction of an imaginary plane which contains each of mountains or valleys of the waveform of the bellows 18 is substantially consistent with the above-mentioned axial direction. In the bellows 18, the transformable wall face is formed to be transformable at intersections of the transformable wall face and a straight light (axial line) passing through the insides of the orifice part 13 and the containing part 12 to penetrate the transformable wall face, and along the straight line direction (axial direction).

The non-transformable portion 17 has a substantially-cylindrical thick-tube portion 21 which is made of a translucent resin such as polypropylene, polyester or polyethylene and can store liquid at the inside thereof, a substantially-cylindrical thin-tube portion 22 which is thinner than the portion 21, and a funnel-form transition portion 23 arranged between the thick-tube portion 21 and the thin-tube portion 22. The orifice part 13 is fitted to the leading end of the thin-tube portion 22. The thin-tube portion 22 is set up by enclosing the carrier particles 14 and 15 into the portion 22, fitting the portion 22 into a fitting portion 24 positioned at the lower end of the transition portion 23, and then unifying the portions by bonding, thermal melting, or the like. The thin-tube portion 22 is suitably made of polypropylene, which is a resin that does not emit fluorescent light when the carrier particles 14 and 15 marked with fluorescent dyes are measured, and has a measure of strength. In the meantime, the transformable portion 16, and a containing part 12 portion which is formed to be integrated with the transformable portion 16 and is a portion other than the tin-tube portion 22 is suitably made of polyester, which has a measure of softness.

The thin-tube portion 22 contains therein the plural carrier particles 14 and 15, the number of which is 20 in this example, in a single-column form. At its upper narrowed portion 25 and its lower narrowed portion 26, the thin-tube portion 22 is narrowed to be made thinner so that liquid can flow out but the carrier particles 14 and 15 cannot flow out. Thus, the carrier particles 14 and 15 are enclosed therein, so as not to flow out from the region of the thin-tube portion. The upper narrowed portion 25 and the lower narrowed portion 26 correspond to the enclosing portion.

The carrier particles 14 and 15 are made of, for example, plural groups each containing carrier particles having a size of about 0.5 mm (two elements or species belong to the groups). At least one of the respective carrier particles which belong to each of the groups of the carrier particles are the carrier particles 14, to which a predetermined chemical substance is bonded or bondable, the carrier particles 14 being marked with a luminescent substance, such as a fluorescent dye or chemically luminescent substance, in order to distinguish the chemical substance. The carrier particles are made of, for example, silica or a fibrous substance such as nylon. The other carrier particles which belong to the groups are the carrier particles 15, which are made of a light-shielding substance for preventing the luminescence from reaching the adjacent carrier particles, for example, an opaque resin or metal. The carrier particles 14 and the carrier particles 15 are arranged to be alternated with each other. Before the carrier particles 14 are introduced into the containing part 12, the carrier particles 14 are distinguishably marked with marking substance different from each other, such as fluorescences different from each other, or with a combination of marking substances different from each other or a molar ratio therebetween.

The following will describe a carrier-enclosed transformable container according to a second embodiment of the invention on the basis of FIG. 2. The same reference numbers as in FIG. 1 represent the same objects. Thus, detailed description thereof is omitted.

As illustrated in FIG. 2(*a*), the carrier-enclosed transformable container, which is a container 27, has a containing part 28 which can contain liquid and gas at its inside surrounded by a wall face, a part of this wall face having a transformable wall face capable of undergoing a predetermined transformation without changing the entire internal surface area of the wall face substantially; an orifice part 29 which is connected to the containing part 28 and can undergo the inflow and outflow of a liquid sucked and discharged by the expansion and contraction of the inside by the transformation of the transformable wall face, respectively; and carrier particles 14 and 15 to which predetermined substances enclosed in the containing part 28 to be in a substantially stationary state are bonded or bondable. The containing part 28 has a single transformable portion 16 surrounded by the transformable wall face, and a non-transformable portion 30 connected to the transformable portion 16, surrounded by a non-transformable wall face, which is not transformable, and connected to the orifice part 29, the inside of the non-transformable portion 30 being permitted to be measured from the outside.

The non-transformable portion 30 has a substantially-cylindrical thick-tube portion 21 which is made of a translucent resin such as polypropylene, polyester or polyethylene and can store liquid at the inside thereof, a substantially-cylindrical thin-tube portion 31 which is thinner than the portion 21, and a funnel-form transition portion 23 arranged between the thick-tube portion 21 and the thin-tube portion 31. The thin-tube portion 31 is set up so as to be freely attached and removed by fitting its upper end into a fitting portion 24 positioned at the lower end of the transition portion 23. The thin-tube portion 31 is suitably made of polypropylene, which is a resin that does not emit fluorescent light when the carrier particles 14 and 15 marked with fluorescent dyes are measured, and has a measure of strength.

As described above, the plural carrier particles 14 and 15, the number of which is 20 in this example, are enclosed, into a single-column form, in the thin-tube portion 31. At the upper side and the lower side thereof, pipes 32 and 33 made of, for example, stainless steel and fitted and inserted into the thin-tube portion 31 are set up, respectively. Regions of the pipes 32 and 33 which can contact the carrier particles have inclined planes 34 and 35, which are obtained by cutting the pipes obliquely to the axial direction, in order not to stuff the pipe 32 or 33 with the carrier particles 14 or 15. A hole in the lower pipe 33 at the lower end thereof corresponds to the orifice part 29.

The following will describe a carrier-enclosed transformable container 36 according to a third embodiment of the invention on the basis of FIG. 3. The same reference numbers as in FIGS. 1 or 2 represent the same objects. Thus, detailed description thereof is omitted.

The carrier-enclosed transformable container 36 has a containing part 37 which can contain liquid and gas at its inside surrounded by a wall face, a part of this wall face having a transformable wall face capable of undergoing a predetermined transformation without changing the entire internal surface area of the wall face substantially; an orifice part 38 which is connected to the containing part 37 and can undergo the inflow and outflow of a liquid sucked and discharged by the expansion and contraction of the inside by the transformation of the transformable wall face, respectively; and carrier particles 14 and 15 to which predetermined substances enclosed in the containing part 41 to be in a substantially stationary state are bonded or bondable. The containing part 41 is composed of transformable portions 39 and 40, and a non-transformable portion, which is a portion other than the portions 39 and 40. The non-transformable portion has a substantially-cylindrical thick-tube portion 42 which is made of a translucent resin such as polypropylene, polyester or polyethylene and can store liquid at the inside thereof, a substantially-cylindrical thin-tube portion 43 which is thinner than the portion 42, and a funnel-form transition portion 44 arranged between the thick-tube portion 42 or the thin-tube portion 43. The orifice part 38 is fitted to the lower end of the thin-tube portion 43. The carrier particles 14 and 15 are put in the thin-tube portion 43. In this example, the thin-tube portion 43 is formed to be integrated with the transition portion 44 and the thick-tube portion 42.

About the two transformable portions 39 and 40 surrounded by the transformable wall face, the individual maximum variable volumes $V_{30}$ and $V_{40}$ of the containing part 37 based on transformations of the transformable wall face in the individual transformable portions 39 and 40, respectively, are different from each other, and $V_{39} \ll V_{40}$. In this case, it is preferred to set the maximum variable volume $V_{40}$ to a value substantially equal to the volume of the space of the thin-tube portion 43 from which the carrier particles 14 and 15 enclosed in the thin-tube portion 43 are excluded.

In the transformable portion 39 having the $V_{39}$, which is the largest maximum variable volume, the transformable wall face is formed to be transformable at intersections of the transformable wall face and a straight light passing through the insides of the orifice part 38 and the containing part 37 to penetrate the transformable wall face, and along the straight line direction (axial direction).

The thin-tube portion 43 is formed to be connected to the transition portion 44 and be integrated with the thick-tube portion 42 and the transition portion 44. The thin-tube portion 43 contains therein the plural carrier particles 14 and 15, the number of which is 20 in this example, in a single-column form. At its upper narrowed portion 45 and its lower narrowed portion 46, the thin-tube portion 43 is narrowed to be made thinner so that liquid can flow out but the carrier particles 14 and 15 cannot flow out. Thus, the carrier particles 14 and 15 are enclosed therein, so as not to flow out from the region of the thin-tube portion. The upper narrowed portion 25 and the lower narrowed portion 26 correspond to the enclosing portion.

On the basis of FIG. 4, the following will describe a photosensor 47 as a light detecting means for measuring optically the carrier particles 14 and 15 enclosed in the thin-tube portion 43 in the carrier-enclosed transformable container 36 according to the third embodiment. The photosensor 47 is suitable for a case where the single carrier-enclosed transformable container 36 is used in the state that the container 36 is supported by a carrier-enclosed head (not illustrated) in a manner that the orifice part 38 is directed downwards and the transformable wall face is transformable and movable in the vertical direction. It is supposed that the carrier particles 14 and 15 to which a fluorescent substance is bonded as a marking material are enclosed, in a single column form, in the thin-tube portion 43 of the carrier-enclosed transformable container 36.

FIG. 4(a) illustrates the photosensor 47, which is to be fitted to the thin-tube portion 43 of the carrier-enclosed transformable container 36. The photosensor 47 is set on a horizontal plane, so as to be permitted to approach the thin-tube portion 43 of the carrier-enclosed transformable container 36 and be separated therefrom.

The photosensor 47 is placed in the carrier-enclosed head. It is supposed that a fluorescent substance is used as a marking substance in the thin-tube portion 43 of the carrier-enclosed transformable container 36. The photosensor 47 can detect the fluorescence, and has the following: semicircular two segments 48 and 49 which be combined into the form of a cylinder wherein a central hole 50 is made, the hole 50 having an inside diameter permitting the thin-tube portion 43 to penetrate the cylinder, and which can be separated from each other along a plane containing the diameter of the cylinder and the axis thereof; an optical fiber 53 which is fitted to the segment 48, has an end face 52 fitted to the inside face of the central hole, and can radiate predetermined excited light rays; and an optical fiber 54 which is fitted to the segment 49, has an end face 51 fitted to the inside face of the central hole, and can receive light rays emitted from the inside of the central hole.

As illustrated in FIG. 4(b), the two segments 48 and 49 of the photosensor 47 are fitted onto a supporting plate (not illustrated) which has, at its center, a hole which the thin-tube portion 43 can penetrate, and can be moved in the vertical direction, so as to cover the hole, whereby the segments 48 and 49 pinch the lower end of the thin-tube portion on the supporting plate in the state that the thin-tube portion 43 penetrates the central hole and the hole.

When the supporting plate (not illustrated) and the photosensor 47 are moved from the lower end of the thin-tube portion 43 relatively upwards to the upper end of the thin-tube portion 43, the thin-tube portion 43 is scanned thereby, so that luminescence from the carrier particles enclosed in the thin-tube portion 43 is measured.

FIG. 5 illustrate a carrier-enclosed transformable container 55 according to a fourth embodiment. The carrier-enclosed transformable container 55 has a containing part 56 which can contain liquid and gas at its inside surrounded by a wall face, a part of this wall face having a transformable wall face capable of undergoing a predetermined transformation without changing the entire internal surface area of the wall face substantially; an orifice part 57 which is connected to the containing part 56 and can undergo the inflow and outflow of a liquid sucked and discharged by the expansion and contraction of the inside by the transformation of the transformable wall face; and carrier particles 14 (the number thereof in this example: 8) to which a predetermined substance enclosed in the containing part 56 to be in a substantially stationary state is bonded or bondable. The containing part 56 has a single transformable portion 67 surrounded by the transformable wall face, and a non-transformable portion 58 connected to the transformable portion 67, surrounded by a non-transformable wall face, which is not transformable, and connected to the orifice part 57, the inside of the non-transformable portion 58 being permitted to be measured from the outside.

In the transformable portion 67, a bellows 59 is formed. In the bellows 59, waves having mountains and valleys made along a direction which traverses the axial direction, as a transformable direction, substantially perpendicularly thereto along the up-and-down direction of the containing part 56 are formed in a wall face surrounding the transformable direction cylindrically. The bellows 59 can be folded or crushed down at the mountains and valleys. The shape of the mountains and valleys of the waves is a closed curve shape contained in an imaginary plane perpendicular to the transformable direction. When an upper end face 60 of the transformable portion 67 is pushed and pressed along the axial direction with a given movable member, the mountains and valleys of the bellows 59 are folded or crushed down so as to contract the transformable portion 67. When the pushing and pressing force is released, the transformable portion is restored into the original state by elastic force of the transformable portion 67.

The non-transformable portion 58 has a thick-tube portion 61, in a substantially rectangular cylindrical form, which is made of a translucent resin such as polypropylene, polyester or polyethylene and can store liquid at the inside thereof, a thin-tube portion 62, in a substantially cylindrical form, which is thinner than the portion 61, and a transition portion 63 arranged between the thick-tube portion 61 and the thin-tube portion 62 and having a step. The shape of the substantially rectangular shape of any cross section of the thick-tube portion 61 perpendicular to the axial direction is, for example, a rectangle having long sides having a length 2 times the length of short sides.

As described above, the plural carrier particles 14, the number of which is 8 in this example, are enclosed, into a single-column form, in the thin-tube portion 62 in such a manner that the carrier particles 14 can contact an introduced liquid. At the upper side and the lower side thereof, short pipes 64 and 65, which each have a sectional shape (sectional shape other than any circle) neither permitting the carrier particles 14 to pass through the pipes nor permitting the pipes to be stuffed with the carrier particles 14, are set up in the thin-tube portion 62, so as to be fitted into the inner wall of the thin-tube portion 62.

FIG. 6 is a perspective view of a carrier-enclosed transformable container processing apparatus 10 according to a fifth embodiment of the invention. The carrier-enclosed transformable container processing apparatus 10 has a carrier enclosed head 70 wherein carrier-enclosed transformable containers 55 according to the third embodiment of the invention, the number of which is two or more (96 in this example), are arranged into the form of two matrix groups each having 12 rows×4 columns so as to direct their orifice parts 57 downwards, the head 79 supporting the containers 55 in such a manner that the orifice parts 57 are not moved or changed by a transformation of the transformable wall faces, and being capable of attaining the suction or discharge of liquid into/from the carrier-enclosed transformable containers 55 simultaneously by transforming the transformable wall faces of the carrier-enclosed transformable containers 55 simultaneously; two micro plates 73 and 74, which are each a container group wherein two or more wells 75 that can contain various liquids such as solution or suspensions are arranged in the form of a matrix of 12 rows×8 columns; and a head moving section (not illustrated) for moving the carrier enclosed head 70 relatively to the two micro plates 73 and 74 as the container groups.

The carrier enclosed head 70 has movable members 71 and 72 which can each contact an entire upper end face 60 of the carrier-enclosed transformable containers 55 arranged in the form of the matrix of 12 rows×8 columns, can each move upwards and downwards, and can each cause the carrier-enclosed transformable containers 55 to be simultaneously transformed and restored (the movable member 71 in FIG. 6 is illustrated in the state that the member 71 is taken off upwards in order to make the arrangement state of the carrier-enclosed transformable containers clear when the member 71 is explained) The movable members 71 and 72 are linked with each other through, for example, nut portions screwed with a ball screen arranged along the vertical direction, and arms. When the ball screw is rotatably driven with a motor, the members can be moved by translational driving of the nut portions along the ball screw. The carrier enclosed head 70 is supported, for example, by placing horizontally two plates each having 48 supporting holes made into the form of the above-mentioned matrix (12 rows×4 columns) at the row interval thereof and the column interval thereof, and then inserting/fitting the carrier-enclosed transformable containers 55 into the individual holes. The shape of the supporting holes has a rectangular hole shape corresponding to the rectangular cylindrical portion of the above-mentioned portion 63 of each of the carrier-enclosed transformable containers 55, and the container is supported by the upper-side step portion thereof. The plates can each be moved, as a part of the carrier enclosed heat 70, vertically and horizontally by the moving section. The carrier enclosed heat 70 can be moved by use of, for example, a separately disposed ball screw.

The group of the carrier-enclosed transformable containers 55, arranged in the matrix form, on the side of the movable member 71 out of the movable members, has a comb-tooth magnet 77 as a magnetizing means for applying a magnetic field to the inside of the thin-tube portion 62 of the non-transformable portion 58 of each of the carrier-enclosed transformable containers 55; and a comb-tooth light-detecting unit 78 as a light detecting means for detecting the state of the carrier particles in each of the carrier-enclosed transformable containers 55. Reference number 79 represents a tray attached and fixed to the carrier enclosed head 70 in order to support the comb-tooth magnet 77 movably in the column direction.

FIG. 7(*a*) is a perspective view illustrating the micro plate 73 (74) having the wells 75 arranged in the form of the matrix of 12 rows×8 columns in detail. The micro plate 73 is a micro plate wherein the wells 75 and 76, the number of which is 96, in the matrix form of 12 rows×8 columns are arranged on a substrate 80. Furthermore, partitions 81, in the form of slender thin plates, are arranged on the surface of the substrate 80 so as to be projected upwards in such a manner that three of the substrates 80 are positioned along the row direction and eleven of the substrates 80 are positioned along the column direction and in such a manner that the substrates 80 cause all the wells to be partitioned into groups each made of a well 75 and a well 76 (out of the wells 75 and 76), the number of which is the natural number "2", the two wells being arranged in the row direction correspondingly to the column interval of the arranged carrier-enclosed transformable containers 55 of the corresponding carrier enclosed head 70.

FIG. 7(*b*) illustrates a first partial well matrix (the wells 75 represented by black circles in the figure) and a second partial well matrix (the wells 76 represented by white circles in the figure), which are each a group of wells into which the orifice parts 57 of all the matrix-form-arranged carrier-enclosed transformable containers 55 of the carrier enclosed head 70 corresponding to the micro plate 73 can be simultaneously inserted. Accordingly, the arrangement of the carrier-enclosed transformable containers 55 of the carrier enclosed head 70 has a matrix corresponding to the arrangement of the first partial well matrix (75, the black circles) and the second partial well matrix (76, the white circles).

Any one group composed of a well 75 and a well 76 adjacent to each other in the up-and-down direction on the figure, out of the wells 75 belonging to the first partial well matrix (75, the black circles) and represented by the black circles and the wells 76 belonging to the second partial well matrix (76, the white circles), is a well group 82 that is a group of wells into which the same container out of the carrier-enclosed transformable container 55 fitted to the corresponding carrier enclosed head 70 can be inserted. Accordingly, the carrier-enclosed transformable containers 55 positioned once in each of areas surrounded by the partitions 81 is not moved over any one of the partitions 81 until the treatment operation about the micro plate 73 (74) is completed.

FIGS. 7(*c*) and (*d*) are views illustrating an example of a micro plate 83 corresponding to a carrier enclosed head according to a different embodiment. The micro plate 83 is a micro plate wherein wells 85, 86, 87 and 88, the number of which is 96, are arranged in a matrix form of 12 rows×8 columns on a substrate 84. Furthermore, partitions 89, in the form of slender thin plates, are arranged on the surface of the substrate 84 so as to be projected upwards in such a manner that three of the partitions 89 are positioned along the column direction and five of the partitions 89 are positioned along the row direction and in such a manner that the partitions 89 cause all the wells to be partitioned into groups 90 each made of a well 85, a well 86, a well 87 and a well 88 (out of the wells 85, 86, 87 and 88), the number of which is the natural number "4", the 4 wells being arranged in the column direction and the row direction correspondingly to the row interval and the column interval of the arranged carrier-enclosed transformable containers 55 of the corresponding carrier enclosed head (not illustrated).

The carrier enclosed head (not illustrated) corresponding to the micro plate 83 is a head having 24 carrier-enclosed transformable containers 55 arranged in the form of a matrix of 6 rows×4 columns, that is, a head wherein six carrier-enclosed transformable containers 55 are arranged in each of four columns, the head being obtained by removing every second container from the 12 carrier-enclosed transformable containers 55 arranged in the column direction in each of the four columns in the carrier enclosed head 70 illustrated in FIG. 6.

As illustrated in FIG. 7(d), the micro plate 83 has a first partial well matrix (wells 85, each represented by a white circle in the figure), a second partial well matrix (wells 86, each represented by a black circle in the figure), a third partial well matrix (wells 87, each represented by a cross in the figure), and a forth partial well matrix (wells 88, each represented by a single-line in the figure), which are each a group of wells into which all the matrix-form-arranged carrier-enclosed transformable containers 55, the number of which is 24, of the corresponding carrier enclosed head (not illustrated) can be simultaneously inserted.

Any one group composed of four wells 85, 86, 87 and 88 out of the wells 85 belonging to the first partial well matrix and represented by the white circles, the wells 86 belonging to the second partial well matrix and represented by the black circles, the wells 87 belonging to the third partial well matrix and represented by the crosses, and the wells 88 belonging to the fourth partial well matrix and represented by the single-lines is a well group 90 into which the same container 55 out of the carrier-enclosed transformable containers 55 fitted to the corresponding carrier enclosed head (not illustrated) can be simultaneously inserted. Accordingly, the carrier-enclosed transformable container 55 positioned once in each of areas surrounded by the partitions 89 is not moved over any one of the partitions 89 until the treatment operation about the micro plate 83 is completed.

In the case of preparing four micro plates equivalent to the micro plate 83 and preparing four bundles each having 24 carrier-enclosed transformable containers 55 arranged into the form of a matrix of 6 row×4 columns, 96 carrier-enclosed transformable containers 55 are totally supplied. The total number of the wells in the micro plates is equal to the number of the wells in the micro plate alone 83. Thus, the number of the wells is different from that in the case of FIG. 6; however, the four micro plates can be simultaneously processed. As a result, the efficiency is high.

FIG. 8(a) is a perspective view illustrating the comb-tooth magnet 77 and the comb-tooth light-detecting unit 78, which are in the state that they are taken out. The comb-tooth magnet 77 is fitted to the carrier enclosed head 70, and has magnets 92 in the form of a matrix of 12 rows×4 columns, the total number of which is 48. The magnets 92 are arranged to be brought into contact with the individual carrier-enclosed transformable containers 55 and separated therefrom, so as to apply a magnetic field simultaneously to the insides of the carrier-enclosed transformable containers 55 and remove the magnetic field.

The comb-tooth magnet 77 has: substantially prismatic comb-tooth members 91 that are arranged in gaps between adjacent columns of the carrier-enclosed transformable containers 55 having a column interval set to a "2" multiple, this number "2" being the natural number of the column interval of the wells 75 and 76, so as to be movable along the column direction, that extend along the column direction, and that are fitted to have a width permitted to be inserted in any one of gaps between adjacent columns of the carrier-enclosed transformable containers 55, the number of the substantially prismatic comb-tooth members 91 being 3, which is (the column number of the carrier-enclosed transformable containers 55-1); two substantially prismatic comb-tooth ends 91a and 91b arranged outside the comb-tooth members 91 and formed to have a slightly larger width than the comb-tooth members 91; a supporting member (not illustrated) connected to single-ends of the comb-tooth members 91 and the comb-tooth ends 91a and 91b and extending in the row direction. Each of the comb-tooth members 91 and the comb-tooth end 91b has magnets 92 arranged along the longitudinal direction thereof, that is, the column direction and at intervals each set to the row interval of the wells 75 and 75, the number of the magnets 92 being the above-mentioned row number (12); and a guide rail 93 arranged along the longitudinal direction of each of the comb-tooth members 91, 91a and 91b, that is, the column direction. The magnets 92 are located on the same sides of the comb-tooth members 91 and the comb-tooth end 91b. The guide rails 93 are positioned on the side farther from the sides. The guide rails 93 guide the comb-tooth light-detecting unit 78 set up movably on the upper surface of the comb-tooth members 91, 91a and 91b.

FIG. 8(b) is a perspective view illustrating a comb-tooth magnet 94 according to a different embodiment, and the above-mentioned comb-tooth light-detecting unit 78. The comb-tooth magnet 94 is fitted to the carrier enclosed head (not illustrated), and has magnets 92 in the form of a matrix of 6 rows×4 columns, the total number of which is 24. The magnets are arranged to be brought into contact with the individual carrier-enclosed transformable containers 55 and separated therefrom, so as to apply a magnetic field simultaneously to the insides of the carrier-enclosed transformable containers 55 and remove the magnetic field. In other words, the magnet is different from the comb-tooth magnet 77 in FIG. 8(a), and the number of the magnets 92 arranged in each of the comb-tooth members and the comb-tooth end is reduced to a half of 12, so that the number of the magnets is six. This corresponds to the above-mentioned carrier enclosed head (not illustrated).

FIG. 9 are views illustrating the comb-tooth light-detecting unit 78 in detail. The comb-tooth light-detecting unit 78 is a unit arranged on the comb-tooth magnet 77 fitted to the carrier enclosed head 70 to be relatively movable to the comb-tooth magnet 77, thereby detecting the states of the insides of the individual carrier-enclosed transformable containers 55.

The comb-tooth light-detecting unit 78 has: substantially prismatic comb-tooth members 95 that are arranged between adjacent ones of the carrier-enclosed transformable containers 55 having a column interval set to a "2" multiple, which is a natural number multiple of the column interval of the wells 75 and 76, so as to be movable along the column direction to the comb-tooth magnet 77 or the carrier-enclosed transformable containers 55, that extend along the column direction, and that are fitted to have a width permitted to be inserted in any one of gaps between adjacent columns of the carrier-enclosed transformable containers 55, the number of the comb-tooth members 95 being 3, which is (the column number of the carrier-enclosed transformable containers 55-1); two substantially prismatic comb-tooth ends 95a and 95b arranged outside of the comb-tooth members 95 and each formed to be slightly wider than each of the comb-tooth members 95; and a supporting member 96 connected to single-ends of the comb-tooth members 95 and the comb-tooth ends 95a and 95b, and extending in the row direction. In each of the comb-tooth members 95 and the comb-tooth ends 95a and 95b, a single light-detecting hole 98 is made along the row direction.

To the light-detecting hole 98 made in any one of the comb-tooth members 95 or the comb-tooth end 95a or 95b is fitted a tip of an optical fiber 99 from a light-emitting unit 100. To the light-detecting hole 98 in the comb-tooth member 95 adjacent to the tip or the comb-tooth end 95a or 95b adjacent to the tip with a slender gap interposed therebetween, the gap being a gap wherein one of the carrier-enclosed transformable container 55 columns is to be arranged, is fitted a tip of an optical fiber 101 connected to an optical sensor 102, so as to face the gap, which is sandwiched between the adjacent two of the comb-tooth members 95 and the comb-tooth ends 95a and 95b.

Reference number 97 represents a slender groove made in each of the comb-tooth members 95 and the comb-tooth ends 95a and 95b along the column direction, so as to be slidably engaged with one of the guide rails 93. The size and the shape of each of the comb-tooth members 95, the comb-tooth ends 95a and 95b and supporting member 96 in the comb-tooth light-detecting unit 78 are the size and the shape corresponding to the comb-tooth magnet 77.

FIG. 10 are views illustrating a carrier-enclosed transformable container 103 according to a sixth embodiment of the invention, which is suitable for being fitted to the carrier enclosed head 70 of the carrier-enclosed transformable container processing apparatus 10. The same reference numbers as in FIG. 1 represent the same objects. Thus, detailed description thereof is omitted.

As illustrated in FIG. 10, the carrier-enclosed transformable container 103 has a containing part 104 which can contain liquid and gas at its inside surrounded by a wall face, a part of this wall face having a transformable wall face capable of undergoing a predetermined transformation without changing the entire internal surface area of the wall face substantially; an orifice part 13 which is connected to the containing part 104 and can undergo the inflow and outflow of a liquid sucked and discharged by the expansion and contraction of the inside by the transformation of the transformable wall face, respectively; and carrier particles 14 and 15 to which predetermined substances enclosed in the containing part 104 to be in a substantially stationary state are bonded or bondable. The containing part 104 has a single transformable portion 107 surrounded by the transformable wall face, and a non-transformable portion 108 connected to the transformable portion 107, surrounded by a non-transformable wall face, which is not transformable, and connected to the orifice part 13, the inside of the non-transformable portion 108 being permitted to be measured from the outside.

In the transformable portion 107, a bellows 109 is formed. The bellows 109 is formed to partition the entire wall face of the containing part 104 or the transformable wall face of the transformable portion 107 into two in a direction which traverses the axial direction of the transformable portion 107 or the containing part 104, which is along the transformable direction. One of the partitions has an apex 110. The other has the non-transformable portion 108; and a flange 111 that is arranged in the boundary between the transformable portion 107 and the non-transformable portion 108, is used to support the carrier-enclosed transformable container 103 onto the carrier enclosed head 70, and has a smaller radius than the transformable portion 107, so as to be projected outwards. In other words, this carrier-enclosed transformable container 103 is used in the state that the container 103 is fitted to the carrier enclosed head 70, and is suitable for automation. The normal line direction of an imaginary plane which contains each of mountains or valleys of the waveform of the bellows 109 is substantially consistent with the above-mentioned axial direction. In the bellows 109, the transformable wall face is formed to be transformable at intersections of the transformable wall face and a straight light (axial line) passing through the insides of the orifice part 13 and the containing part 104 to penetrate the transformable wall face, and along the straight line direction (axial direction).

The non-transformable portion 108 has the same thick-tube portion 21, thin-tube portion 22 and transition portion 23 as described. The thin-tube portion 22 is set up by enclosing the carrier particles 105 and 106 into the portion 22 to enclose the carrier particles into the portion 22, fitting the portion 22 into a fitting portion 24 positioned at the lower end of the transition portion 23, and then unifying the portions by bonding, thermal melting, or the like. The thin-tube portion 22 is suitably made of polypropylene, which is a resin that does not emit fluorescent light when the carrier particles 105 and 106 marked with fluorescent dyes are measured, and has a measure of strength.

FIG. 11 are views illustrating a carrier-enclosed transformable container 113 according to a seventh embodiment of the invention. As illustrated in FIG. 11, the carrier-enclosed transformable container 113 has a containing part 114 which can contain liquid and gas at its inside surrounded by a wall face, a part of this wall face having a transformable wall face capable of undergoing a predetermined transformation without changing the entire internal surface area of the transformable face substantially; an orifice part 13 which is connected to the containing part 114 and can undergo the inflow and outflow of a liquid sucked and discharged by the expansion and contraction of the inside by the transformation of the transformable wall face, respectively; a rodlike carrier 118 having plural bonding moieties 115 to which predetermined substances enclosed in the containing part 114 to be in a substantially stationary state are bonded or bondable. The containing part 114 has a single transformable portion 107 surrounded by the transformable wall face, and a non-transformable portion 120 connected to the transformable portion 107, surrounded by a non-transformable wall face, which is not transformable, and connected to the orifice part 13, the inside of the non-transformable portion 120 being permitted to be measured from the outside.

As illustrated in FIG. 11, in the rodlike carrier 118, plural the bonding moieties 115, to which plural chemical material species are bonded or bondable, are partitioned by the boundary 116 with a hydrophobic material, such as oily ink, positioned between the bonding moieties 115. In its thin-tube portion 117, the rodlike carrier 118 is contained in a single-column form along the vertical direction. At each of its upper narrowed portion 25 and its lower narrowed portion 26, a small pipe 119 is fitted into the thin-tube portion 117 so as to make the thin-tube portion 117 narrow. Thus, liquid can flow out, but the rodlike carrier 118 is enclosed not to flow out. The upper narrowed portion 25, the lower narrowed portion 26 and the two pipes 119 correspond to the enclosing portion.

FIG. 12 are views illustrating a carrier-enclosed transformable container 121 according to an eighth embodiment of the invention, which is suitable for being fitted to the carrier enclosed head 70 of the carrier-enclosed transformable container processing apparatus 10.

As illustrated in FIG. 12, the carrier-enclosed transformable container 122 has a containing part 122 which can contain liquid and gas at its inside surrounded by a wall face, a part of this wall face having a transformable wall face capable of undergoing a predetermined transformation without changing the entire internal surface area of the wall face substantially; an orifice part 123 which is connected to the containing part 122 and can undergo the inflow and outflow of a liquid sucked and discharged by the expansion and contraction of the inside by the transformation of the transformable wall face, respectively; and carrier spheres 124 to which predetermined substances enclosed in the containing part 122 to be in a substantially stationary state are bonded or bondable. The containing part 122 has a single transformable portion 125 surrounded by the transformable wall face; and a non-transformable portion 126 that has the enclosed carrier spheres 124 and is connected to the transformable portion 125, surrounded by a non-transformable wall face, which is not transformable, and connected to the orifice part 123, the inside of the non-transformable portion 126 being permitted to be measured from the outside.

A bellows 127 is formed in the transformable wall face of the transformable portion 125. The bellows 127 is formed to partition the entire wall face of the containing part 122 or the transformable wall face of the transformable portion 125 into two in a direction which traverses the axial direction of the transformable portion 125 or the containing part 122, which is along the transformable direction. At the upper end of the upper region thereof, which is one of the partitions, an introducing hole 129 is made in order that the carrier spheres 124 may be introduced into the containing part 122. The introducing hole 129 is closed by attaching a cover 128 to a flange around the introducing hole 129 by bonding or thermal welding after the carriers spheres 124 are introduced into the hole.

The lower region, which is the other, has the non-transformable portion 126; and a flange 130 that is arranged in the boundary between the transformable portion 125 and the non-transformable portion 126, is used to support the carrier-enclosed transformable container 121 onto the carrier enclosed head 70, and has a smaller radius than the transformable portion 125, so as to be projected outwards. In other words, this carrier-enclosed transformable container 121 is used in the state that the container 121 is fitted to the carrier enclosed head 70, and is suitable for automation. The normal line direction of an imaginary plane which contains each of mountains or valleys of the waveform of the bellows 127 is substantially consistent with the above-mentioned axial direction. In the bellows 127, the transformable wall face is formed to be transformable at intersections of the transformable wall face and a straight light (axial line) passing through the insides of the orifice part 123 and the containing part 122 to penetrate the transformable wall face, and along the straight line direction (axial direction).

The non-transformable portion 126 has a substantially-cylindrical thick-tube portion 131 which is made of a translucent resin such as polypropylene, polyester or polyethylene and can store liquid at the inside thereof, a substantially-cylindrical thin-tube portion 132 which is thinner than the portion 131, and a funnel-form transition portion 133 arranged between the thick-tube portion 131 and the thin-tube portion 132. The orifice part 123 is fitted to the leading end of the thin-tube portion 132. Plural carrier spheres are enclosed, as a particulate filler for chromatography, in the thin-tube portion 131. The carrier spheres can capture the above-mentioned predetermined substances by adsorption or the like, and each have a larger diameter than the inside diameter of the thin-tube portion 132. The transition portion 133 has an elliptic cross-section perpendicular to the axial direction so as not to be stuffed with the carrier spheres 124. The "filler" is an insoluble stationary phase filled into a predetermined container and selected in order to attain the adsorption of a target biological substance contained in a given fluid as the so-called movable phase on the basis of the principle of liquid chromatography.

FIG. 13 are views illustrating a carrier-enclosed transformable container 134 according to a ninth embodiment of the invention, which is suitable for being fitted to the carrier enclosed head 70 of the carrier-enclosed transformable container processing apparatus 10. The same reference numbers as in FIG. 12 represent the same objects as in FIG. 12. Thus, detailed description thereof is omitted.

As illustrated in FIG. 13, the carrier-enclosed transformable container 134 has a containing part 135 which can contain liquid and gas at its inside surrounded by a wall face, a part of this wall face having a transformable wall face capable of undergoing a predetermined transformation without changing the entire internal surface area of the wall face substantially; an orifice part 123 which is connected to the containing part 135 and can undergo the inflow and outflow of a liquid sucked and discharged by the expansion and contraction of the inside by the transformation of the transformable wall face, respectively; a carrier sphere 136 to which a predetermined substance enclosed in the containing part 135 to be in a substantially stationary state is bonded or bondable. The containing part 135 has a single transformable portion 125 surrounded by the transformable wall face, and a non-transformable portion 139 that has the enclosed carrier sphere 136 and is connected to the transformable portion 125, surrounded by a non-transformable wall face, which is not transformable, and connected to the orifice part 123, the inside of the non-transformable portion 139 being permitted to be measured from the outside.

The non-transformable portion 139 has a substantially-cylindrical thick-tube portion 140 which is made of a translucent resin such as polypropylene, polyester or polyethylene and can store liquid at the inside thereof, a substantially-cylindrical thin-tube portion 132 which is thinner than the portion 140, and a funnel-form transition portion 133 arranged between the thick-tube portion 140 and the thin-tube portion 132. The orifice part 123 is fitted to the leading end of the thin-tube portion 132. The carrier sphere 136 is enclosed as a filler as described above in the thick-tube portion 140. The carrier can capture the above-mentioned predetermined substance by adsorption or the like, and each have a far larger diameter than the inside diameters of the thin-tube portion 132 and the transition portion 133. The carrier sphere 136 is supported by two convex points 137 and 138, which are positioned on a wall face of the thick-tube portion 140 and slightly projected inwards in the state that the points oppose to each other across the axial line of the thick-tube portion 140. The convex points 137 and 138 are formed in such a manner that the thick-tube portion 140 is pushed from the outside thereof. For this reason, in the diameter direction obtained by rotating the diameter direction along which the two convex portions are jointed to each other, horizontally, at an angle of 90 degrees, gaps are made between the carrier sphere and the inner wall face of the thick-tube portion 140. Thus, liquid can pass through the gaps.

The following will describe a case where a carrier-enclosed transformable container processing method according to a tenth embodiment is applied to SNP-detecting reaction using the carrier-enclosed transformable container processing apparatus 10 according to the fifth embodiment.

As illustrated schematically in FIG. 14, the method is a method used to detect a polymorphic base (of one out of two types herein) of SNPs (Single Nucleotide Polymorphisms) of four positions of genes (ATase exon 6, ATase exon 8, CYP2C19 exon 5, and CYP2D6 exon 1) of specimens collected from 96 examinees. This processing has a sample preparing step S1 as a preparation step of extracting the genes of the specimens, amplifying the genes, and preparing ASPE products by the ASPE method, which will be described later; an enclosing step S2 of bonding tag DNAs, which will be described later, as detecting probes to carrier particles 14 to be enclosed into the carrier-enclosed transformable containers 55 to prepare plural carrier particle 14 species (8 species in this example), and then enclosing the species into each of the carrier-enclosed transformable containers 55; a bonding reaction step S3 of conducting bonding-reaction between the carrier particles 14 and the ASPE products; and a detecting step S4 of detecting results of the bonding reaction.

As illustrated in FIG. 14(a), the sample preparing step S1 has, for example, a collecting step of collecting specimens, such as mouth mucosae, bloods or nails, from the 96 examinees; an amplifying step of extracting DNAs contained in the mouth mucosae or the like, and amplifying the DNAs by the PCR process; a purifying step of purifying the DNAs; and an ASPE product preparing step of using the ASPE, which will be described later, to prepare ASPE products from the purified DNAs.

In the collecting step, liquids wherein the mouth mucosae or the like collected from the 96 examinees are suspended are held in the micro plate (not illustrated), which has 96 wells (not illustrated). The carrier-enclosed transformable containers 55 in which no carrier is contained are fitted to the carrier enclosed head 70, and a suspension of magnetic particles the surfaces of which are covered with a porous substance, silica or some other substance is sucked, transferred and then discharged/injected simultaneously into each of the wells (not illustrated).

The movable members 71 and 72 are moved upwards and downwards, thereby repeating suction and discharge so as to bond the DNAs onto the magnetic particles. In this way, the DNAs are captured. The comb-tooth magnet 77 is shifted closely to the individual transformable containers, so that a magnetic field is applied into the insides thereof. In this state, the movable members 71 and 72 are moved upwards and downwards, thereby adsorbing the magnetic particles, on which the DNAs are captured, onto the inner walls of the individual transformable containers, so as to be separated. From the separated magnetic particles, on which the DNAs are captured, the DNAs are released so as to be extracted. The DNAs are held into the individual wells in the micro plate.

Next, predetermined primers are used to amplify the extracted DNAs by the PCR process in such a manner that the above-mentioned four DNAs are yielded, and then the amplified products are held into the individual wells, the number of which is 96. In order to remove impurities containing residues of the primers, the mouth mucosae and others, new transformable containers are fitted to the carrier enclosed head 70 and the movable members 71 and 72 are used to move the containers upwards and downwards, thereby causing a new suspension of magnetic particles to be sucked into each of the wells wherein the suspensions of the amplified DNAs are held and be discharged therefrom. In this way, the DNAs are captured onto the magnetic particles, and then the comb-tooth magnet 77 is used to apply a magnetic filed to the insides of the transformable containers 55, so as to cause the magnetic particles to be adsorbed onto the inner walls of the transformable containers 55, separated and purified.

Next, the ASPE (Allele-specific primer extension process) is used to prepare an ASPE product 148 for deciding the SNP of the above-mentioned four positions about the gene of each of the specimens.

As illustrated in FIG. 14(b), there is prepared, as a primer, a synthetic DNA consisting of single-stand several ten of base designed to have at its 3' terminal a base sequence 144 complementary to a base sequence 143 of a single-stand tag DNA 142, which will be described later, have at its 5' terminal the base 145 of the SNP, and have a base sequence complementary to a sequence closest to the SNP of each of the above-mentioned four genes between the base sequence 144 and the base 145. Such primers are synthesized in accordance with possible polymorphic species; in this case, two type primers for each of the four genes, totally, eight type primers are synthesized. Each of the primers contains one of the tag DNAs 142 having eight predetermined base sequences different from each other, and the base of the corresponding SNP. Using the primers, and Dig-dUTP 146 instead of the base "T", extension and amplification are performed on the basis of each of the genes of each of the specimens by the PCR process. As a result, about only the primers corresponding to the polymorphic species of the DNAs of each of the specimens, extension and amplification are attained, so that the ASPE product 148 is prepared for each of the 96 specimens.

The prepared ASPE products 148 are held in the well groups in the first partial matrixes, to which the wells 75 (the black circles) belong, in the micro plates 73 and 73. On the other hand, a washing solution to be used in the detecting step S4, which will be described later, is held in the well groups in the second partial matrixes, to which the well 76 (the white circles) belong, in the micro plates 73 and 74. Furthermore, in two other equivalent micro plates not illustrated, the AP-marked anti-Dig antibody 147, which is bonded specifically to Dig-dUTP 146, is held in their first partial matrixes, and a substrate solution 149 (CDP-Star) is held in their second partial matrixes.

In this example, a mixture wherein all of the eight ASPE product 148 species are mixed for each of the specimens is held in each of the wells 75. However, for example, the following four micro-plate-groups may be prepared to attain the processing: micro plates 73 and 74 wherein a mixture obtained by mixing two species out of the ASPE product 148 species is held in their first partial matrixes and the above-mentioned substrate solution is held in their second partial matrixes; and other necessary micro-plate-groups.

In the step S2, carrier particles 14 to be contained in the carrier-enclosed transformable containers 55 are formed and enclosed therein. As illustrated in FIG. 14(b), the carrier particles 14 to be formed are, for example, carrier particles each covered with avidin 141 and each having the bonded tag DNA 142, the DNA 142 having a predetermined biotinyl base sequence 143. The carrier particles 14 used may be made of various resins, such as nylon (manufactured by Polysciences Co, the diameter of which is, for example, about 1 mm. Besides, for example, a ceramic (alumina manufactured by Chiba Ceramic MFG. Co., Ltd.; diameter: 1.88 mm) may be used. In the case of using the above-mentioned light-shielding particles, for example, a color glass having a diameter of 2.0 mm is used.

The base sequences 143 of the individual tag DNAs 142, as well as the individual complementary base sequences 144 incorporated into the primers, are synthesized to have different base sequences 143, as well as different base sequences 144, in accordance with bases of possible polymorphs of the SNP of the individual genes. As a result, in the processing according to the present embodiment, about the SNP of the four positions, eight base sequence 143 species and eight base sequence 144 species are required for possible polymorphic base species, the species being two species for each of the four positions. Thus, eight carrier particle 14 species are formed. For example, the first carrier particles and the second carrier particles are carrier particles corresponding to the gene ATase exon 6 wherein Tag 1 (base C) and Tag 3 (base T) are used, respectively, as the tag DNAs 142. The third carrier particles and the forth carrier particles are carrier particles corresponding to the gene ATase exon 8 wherein Tag 4 (base A) and Tag 2 (base G) are used, respectively, as the tag DNAs 142. The fifth carrier particles and the sixth carrier particles are carrier particles corresponding to the gene CYP2C19 exon 5 wherein Tag 7 (base A) and Tag 6 (base G) are used, respectively, as the tag DNAs 142. The seventh carrier particles and the eighth carrier particles are carrier particles corresponding to the gene CYP2D6 exon 1 wherein Tag 9 (base C) and Tag 10 (base T) are used, respectively, as the tag DNAs 142.

The thus-formed eight carrier particles 14 species, to which the tag DNAs 142 having the eight predetermined biotinyl base sequences 143 are bonded, are arranged in a predetermined order, i.e., in the order of from the first carrier particles to the eighth carrier particles. The resultant is enclosed into each of the carrier-enclosed transformable containers 55, so as to produce 96 carrier-enclosed containers. These are set, in a matrix form, to the carrier enclosed head 70. In order to enclose the carrier particles 14, for example, the short pipes 64 and 65 are fitted into the upper region and the lower region of the arrangement of the thin-tube portions 62 of the individual carrier-enclosed transformable containers 55. The 96 carrier-enclosed transformable containers 55, in which the carrier particles 14 of the plural species are enclosed, are arranged to be divided into two matrixes each having 12 rows×4 columns. In the case of making the plural carrier particle species so as to be distinguishable from each other using marking substances in accordance with the individual species, it is not especially necessary to decide the arrangement order of the carrier particles in each of the thin-tube portions 62. In the case of using light-shielding particles, for example, carrier particles for reaction and the light-shielding particles are arranged to be alternated with each other.

As the thin-tube portions 62, for example, the thin-tube portions 62 made of polypropylene are used. The size of the thin-tube portions 62 is as follows: in the case of using, for example, ceramic carrier particles having a diameter of 1.0 mm as the carrier particles, for example, thin-tube portion in the form of a circle 1.1 mm in diameter are used; and in the case of using ceramic carrier particles having a diameter of 1.88 mm, for example, thin-tube portions in the form of a circle 2.0 mm in diameter are used. Furthermore, in the case of using glass beads 2.0 mm in diameter as the light-shielding particles, thin-tube portions in the form of a circle 2.2 mm in diameter are used.

In the step S3, a moving unit (not illustrated) is used to move the individual orifice parts 57 of the two groups of the carrier-enclosed transformable containers 55 arranged in the matrix form in the carrier enclosed head 70 to positions wherein the orifice parts 57 can be inserted to the first partial matrixes made of the wells 75 in the micro plates 73 and 74. Next, by means of the moving unit (not illustrated), the orifice parts 57 are simultaneously inserted into the individual wells 75 in the micro plates 73 and 74. About the transformation of each of the carrier-enclosed transformable containers 55, a predetermined standard position is set, and then with reference to the standard position, the transformation of the transformable wall face is controlled. Specifically, in the standard state thereof, the position of the movable members 71 and 72 is in the state that the position contacts the upper end face 60. In the case of representing the maximum internal volume of the transformable container and the minimum interval volume thereof by $V_1$ and $V_2$, respectively, the volume $V_0$ in the standard state is decided to satisfy the following: $V_1-V_0 \leq V_0-V_2$, that is, $(V_1+V_2)/2 \leq V_0$. In this way, the standard volume is set to make the suction volume $(V_1-V_0)$ smaller than the discharge volume $(V_0-V_2)$, thereby making it possible to prevent the volume of a sucked liquid from remaining in the carrier-enclosed transformable container 55. In other words, the movable members 71 and 72 are in the state that the upper end faces 60 press the carrier-enclosed transformable containers 55 to set the internal volume of each of the carrier-enclosed transformable containers 55 into $V_0$.

Next, the orifice parts 57 are inserted into the wells 75 corresponding to the first partial matrixes, which belong to the individual wells 75 in the micro plates 73 and 74, and then the movable members 71 and 72 are moved upwards, thereby sucking the mixed liquids of the ASPE products 148 contained in accordance with the individual specimens into the individual carrier-enclosed transformable containers 55. In this way, the liquids are each brought into contact with each of the carrier particle 14 species, thereby causing hybridization reaction between the base sequence 143 of the tag DNA 142 and the base sequence 144 complementary to the base sequence 143 of the ASPE product 148. In a case where in accordance with the individual carrier particle 14 species the corresponding parts of the ASPE product 148 are present, the parts of the ASPE product 148 are bonded thereto.

Next, in the step S4, the moving unit (not illustrated) is used to move the carrier enclosed head 70 up to the second partial matrixes in the micro plates 73 and 74, wherein the washing solution is contained, along the row direction, on the above-mentioned moving path, by the column interval, so as to position the orifice parts 57 to the wells 76 belonging to the second partial matrixes, and then the orifice parts 57 are simultaneously inserted thereinto. Next, the movable members 71 and 72 are used to move the orifice parts upwards and downwards from the standard position, thereby repeating suction and discharge to wash the ASPE products. Thereafter, the carrier enclosed head 70 is moved to the micro plate (not illustrated) wherein the AP-marked anti-Dig antibody 147, which is bonded specifically to the Dig-dUTP 146, is contained, so as to position the orifice parts 57 to the wells (not illustrated) belonging to the first partial matrixes. Then, the orifice parts 57 are simultaneously inserted thereinto. The movable members 71 and 72 are used to repeat suction and discharge, thereby bonding the Dig-dUTP 146 to the AP-marked anti-Dig antibody 147. As a result, only about one or more species corresponding to existing polymorphs, out of the individual carrier particle 14 species of each of the specimens, the ASPE product 148 part(s) to which the AP-marked anti-Dig antibody 147 is bonded is/are bonded to the carrier particles 14. Preferably, the resultant is further washed with a washing solution, and then the moving unit (not illustrated) is used to move the carrier enclosed head 70 along the row direction, on the above-mentioned moving path, by the column distance, thereby positioning the orifice parts 57 to the wells (not illustrated) belonging to the second partial matrixes. Then, the orifice parts 57 are simultaneously inserted thereinto. Next, the movable members 71 and 72 are used to move the orifice parts upwards and downwards from the standard position, thereby repeating the suction of the substrate solution 149 into the carrier-enclosed transformable containers 55 and the discharge thereof from the containers 55. In this way, the substrate solution 149 is caused to react with the Dig to cause chemical luminescence. At this time, the comb-tooth light-detecting unit 78 set to the carrier enclosed head 70 is used to detect luminescence from the enclosed carrier particles 14. The detection of the chemical luminescence is attained by repeating a matter that light rays from the carrier particles 14 are received by the optical fibers 101 in accordance with individual carrier particles 14 by moving the comb-tooth members 95 and the comb-tooth ends 95*a* and 95*b* in the comb-tooth light-detecting unit 78 successively along the column direction to shift the light-detecting holes 98 successively for the respective carrier-enclosed transformable container 55 rows, the number of which is four, and further moving the carrier-enclosed transformable containers 55 upwards. A result obtained by measuring the genes from certain one out of the specimens is shown as a photograph in the step S4 in FIG. 14. About the genes of this specimen, only very weak light rays are detected from the first, sixth and seventh carrier particles. It is understood from this matter that about the SNP of the gene ATase exon 6 of this specimen, the polymorphic base is T, about the SNP of the gene ATase exon 8 thereof, the polymorphic bases are A/G, about the SNP of the gene CYP2C19 exon 5 thereof, the polymorphic base is A, and about the SNP of the gene CYP2D6 exon 1 thereof, the polymorphic base is T.

The embodiments which have been described above are embodiments which have been specifically described in order to make the invention more understandable. Other embodiments are acceptable. Accordingly, the embodiments can be varied or modified as far as the subject matter of the invention is not changed. For example, in the above-mentioned embodiments, transformation is attached mainly of some of bellows. However, transformation can be realized by, for example, a transformable wall face having a form other than bellows, or using an elastomer such as rubber as the material of the transformable wall face. Moreover, the shape of the carrier-enclosed transformable container is not limited to the above-mentioned shapes, either. Thus, the shape may be a shape having a step in a thick-tube portion or thin-tube portion.

The configuration of carrier-enclosed transformable containers in a carrier enclosed head is not limited to the above-mentioned configurations. The configuration is, for example, a configuration wherein 4, 6, 8, 12, 96 or 384 containers are arranged in a single-column form or a matrix form. As the processing, only the detection of SNPs using hybridization about DANs has been described. However, the processing is not limited thereto, and the apparatus may be used, for example, for detecting a protein using an antigen-antibody reaction. Moreover, only the case has been described wherein a processing is conduced using two carrier enclosed heads each using one movable member for 48 carrier-enclosed transformable containers, and four micro plates each having 96 wells; however, the processing of the invention is not limited to this case. For example, the following processing may also be conducted: a processing using four carrier enclosed heads each using one movable member for 24 carrier-enclosed transformable containers, and eight micro plates each having 96 wells.

[Industrial Applicability]

The carrier-enclosed transformable container, the carrier-enclosed transformable container processing apparatus and the carrier-enclosed transformable container processing method according to the invention are related to fields in which treatments of one or more solutions containing various biogenic substances or the like are required, for example, the industrial field, the agricultural field for foods, farm products, processed and marine products and others, the pharmaceutical field, the medical field in which hygiene, health, immunity, diseases, heredity, and others are handled, the chemical or biological field, and any other field. The invention is in particular useful for cases where a series of treatments using many reagents or substances are continuously conducted in a predetermined order.

Explanation of Reference Numbers

10 carrier-enclosed transformable container processing apparatus

Figure 1:
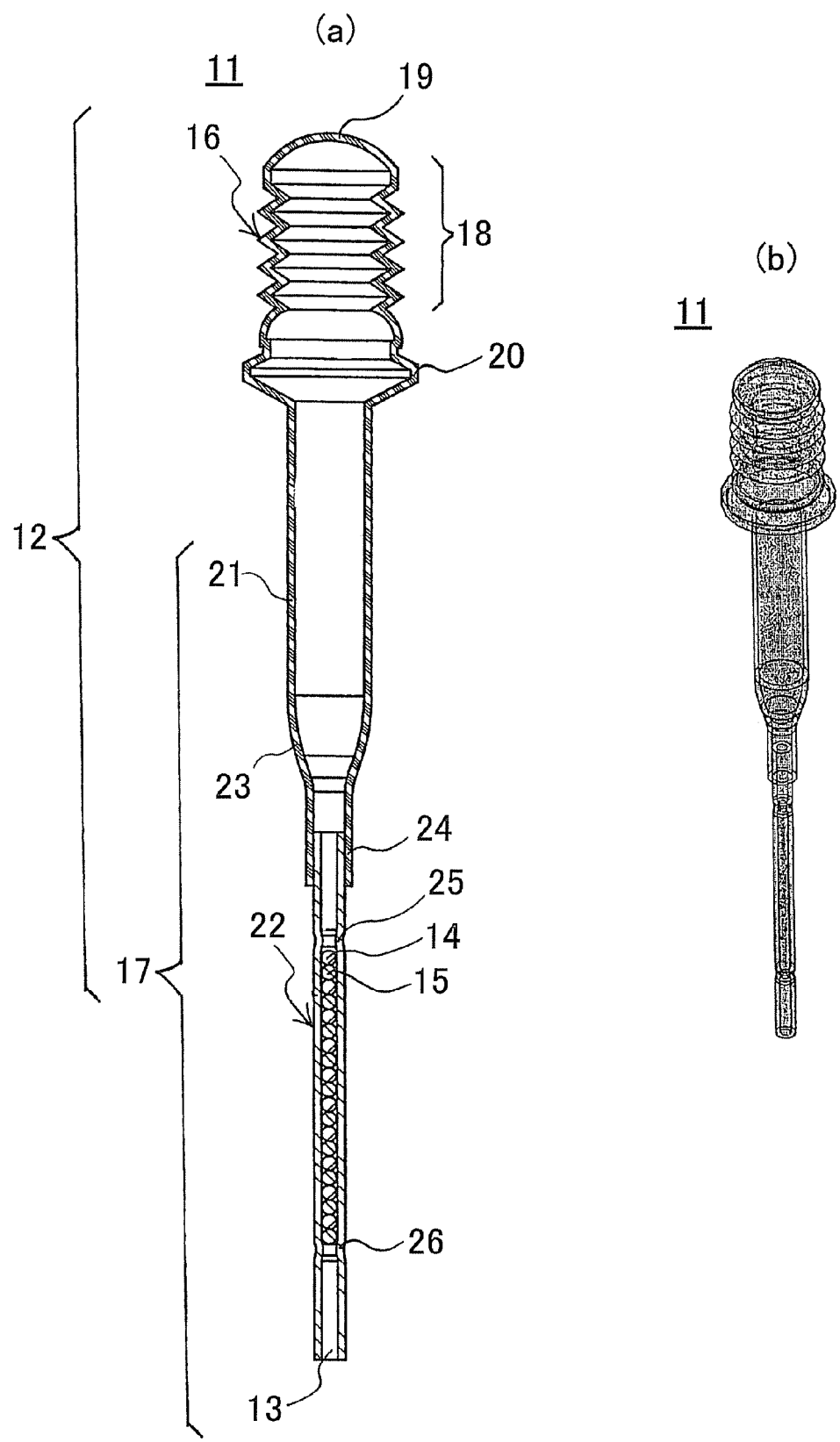
FIG. 1 are a sectional view and a perspective view illustrating a carrier-enclosed transformable container according to a first embodiment of the invention.
Figure 2:
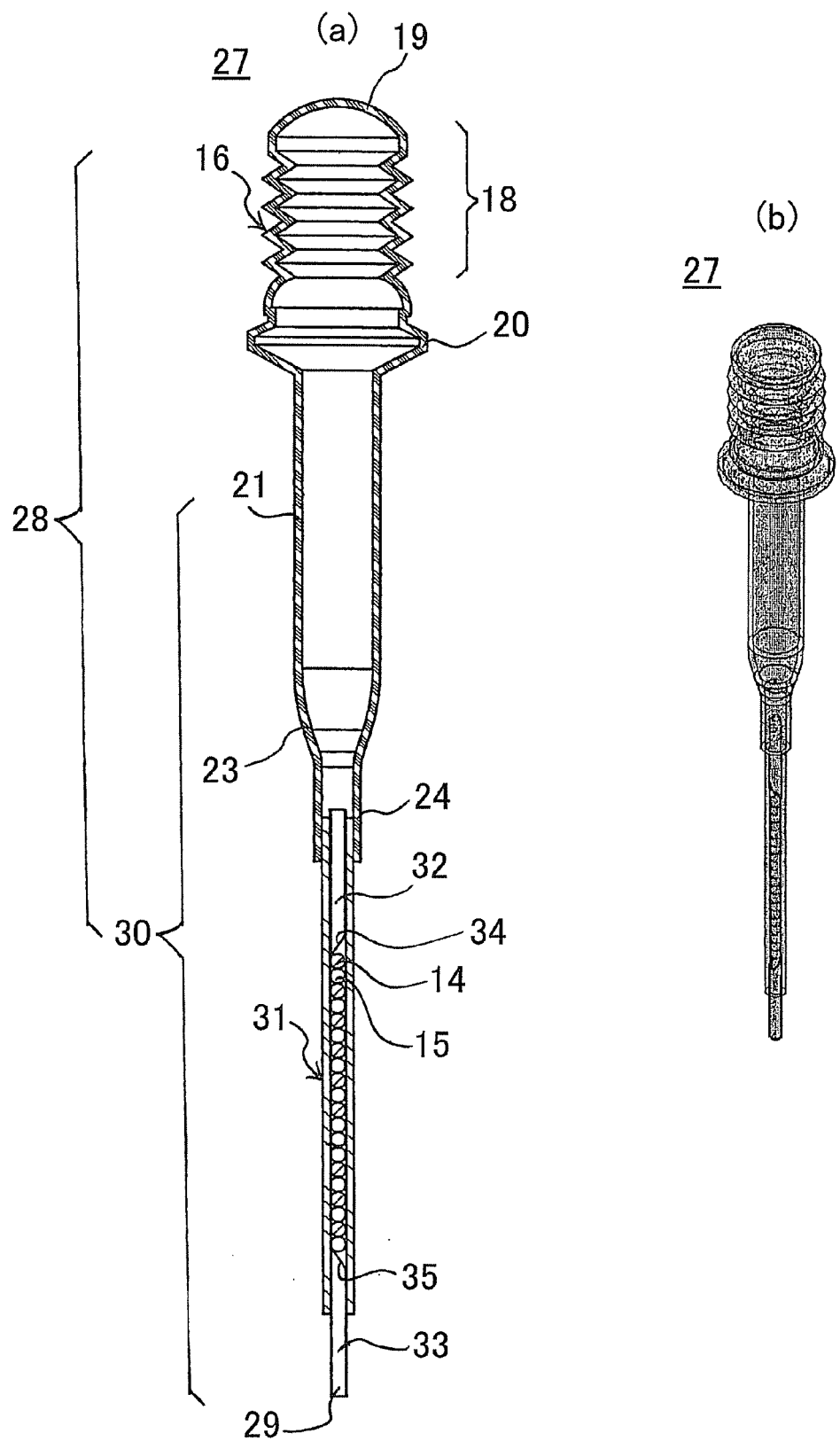
FIG. 2 are a sectional view and a perspective view illustrating a carrier-enclosed transformable container according to a second embodiment of the invention.
Figure 3:
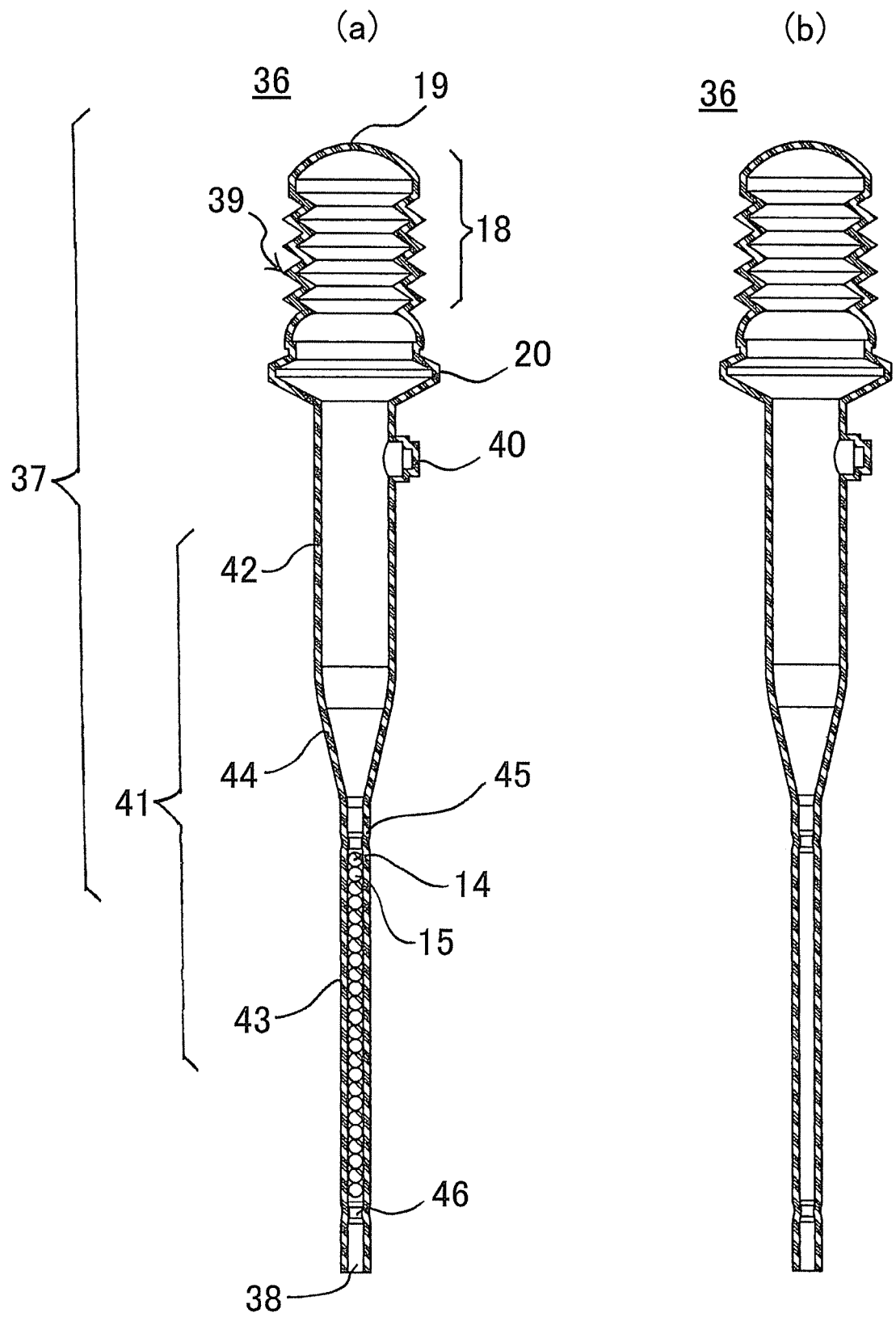
FIG. 3 are a sectional view and a perspective view illustrating a carrier-enclosed transformable container according to a third embodiment of the invention.
Figure 4:
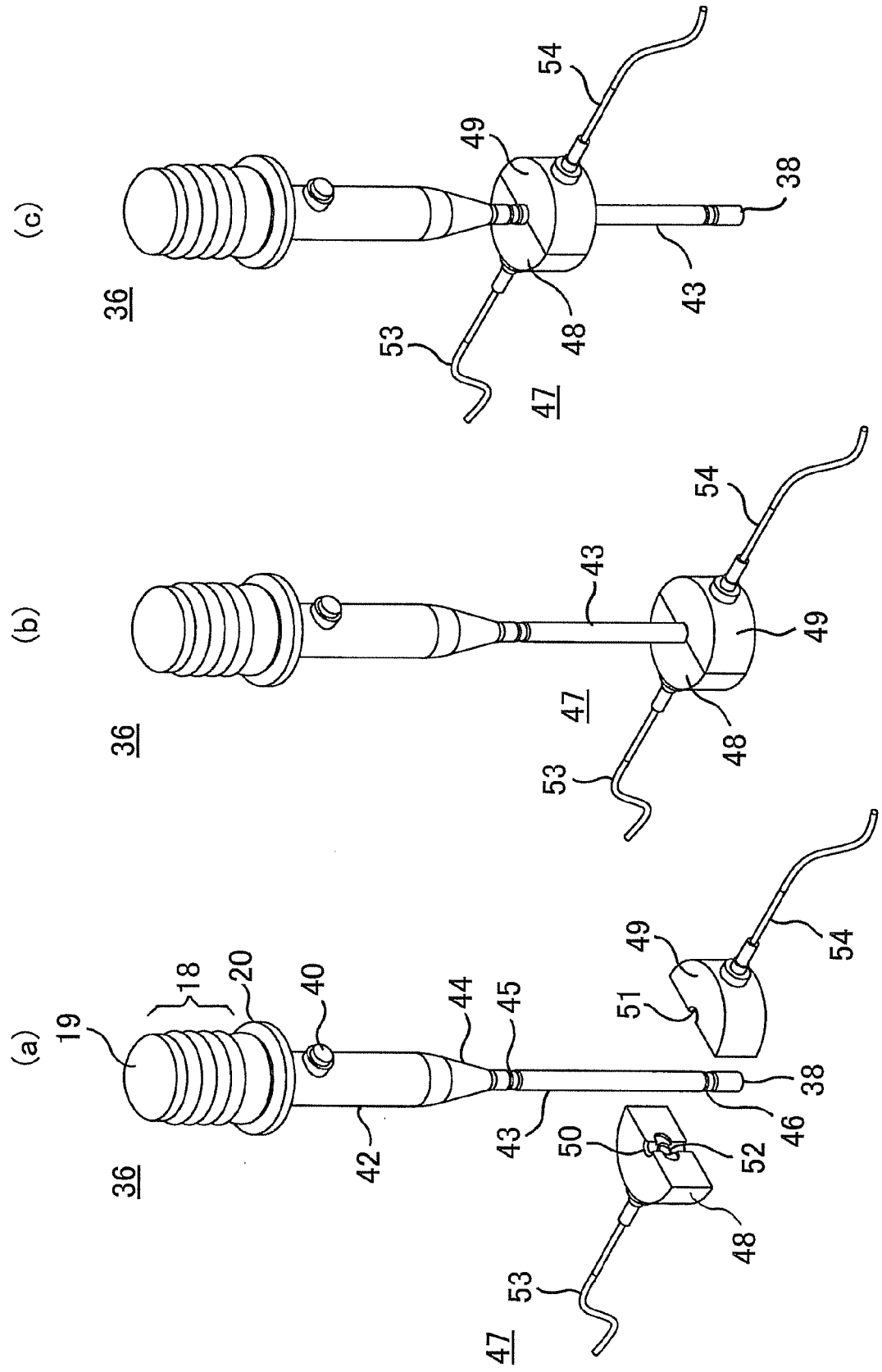
FIG. 4 are each a perspective view illustrating a photosensor applied to the carrier-enclosed transformable container according to the third embodiment of the invention.
Figure 5:
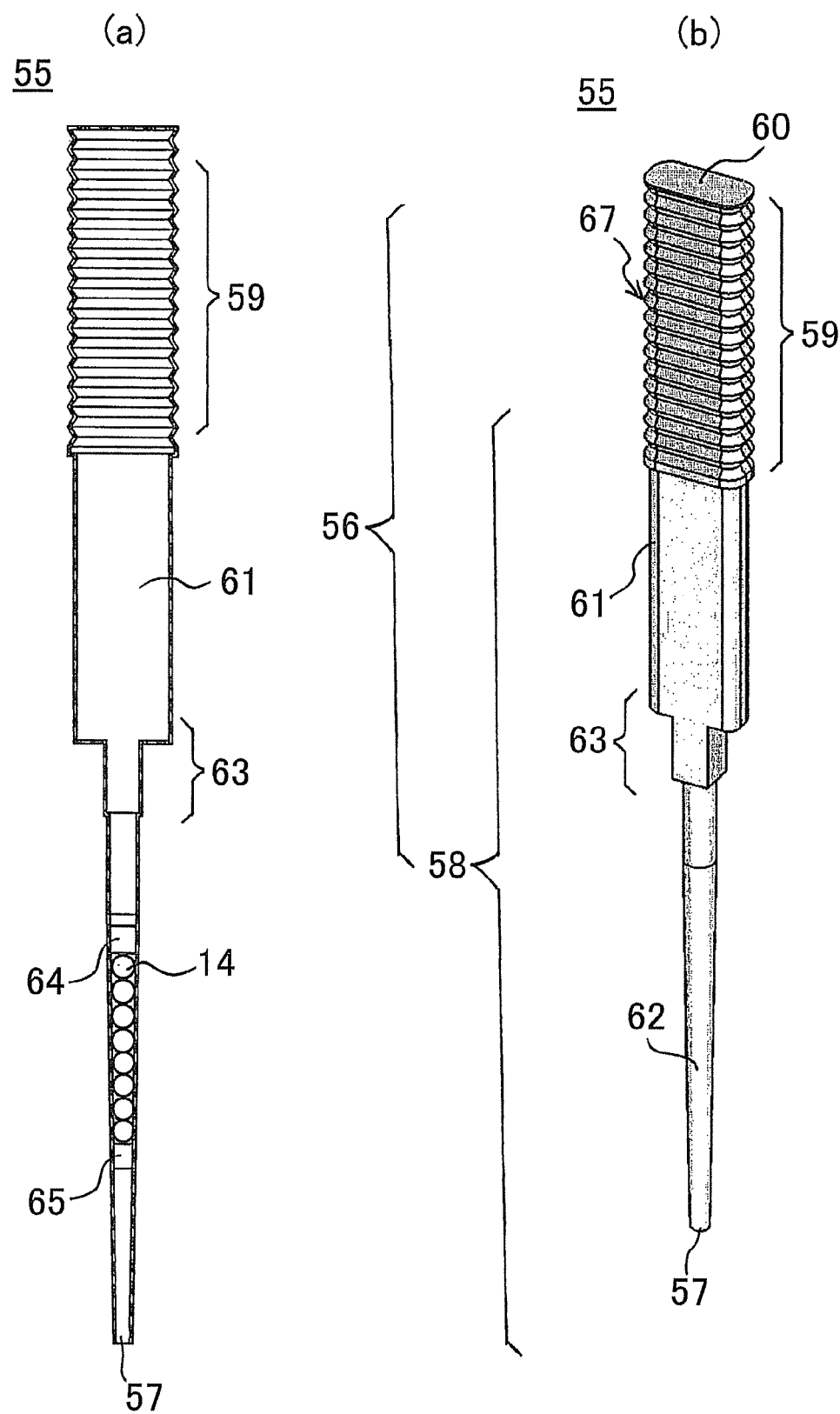
FIG. 5 are a sectional view and a perspective view illustrating a carrier-enclosed transformable container according to a fourth embodiment of the invention.
Figure 6:
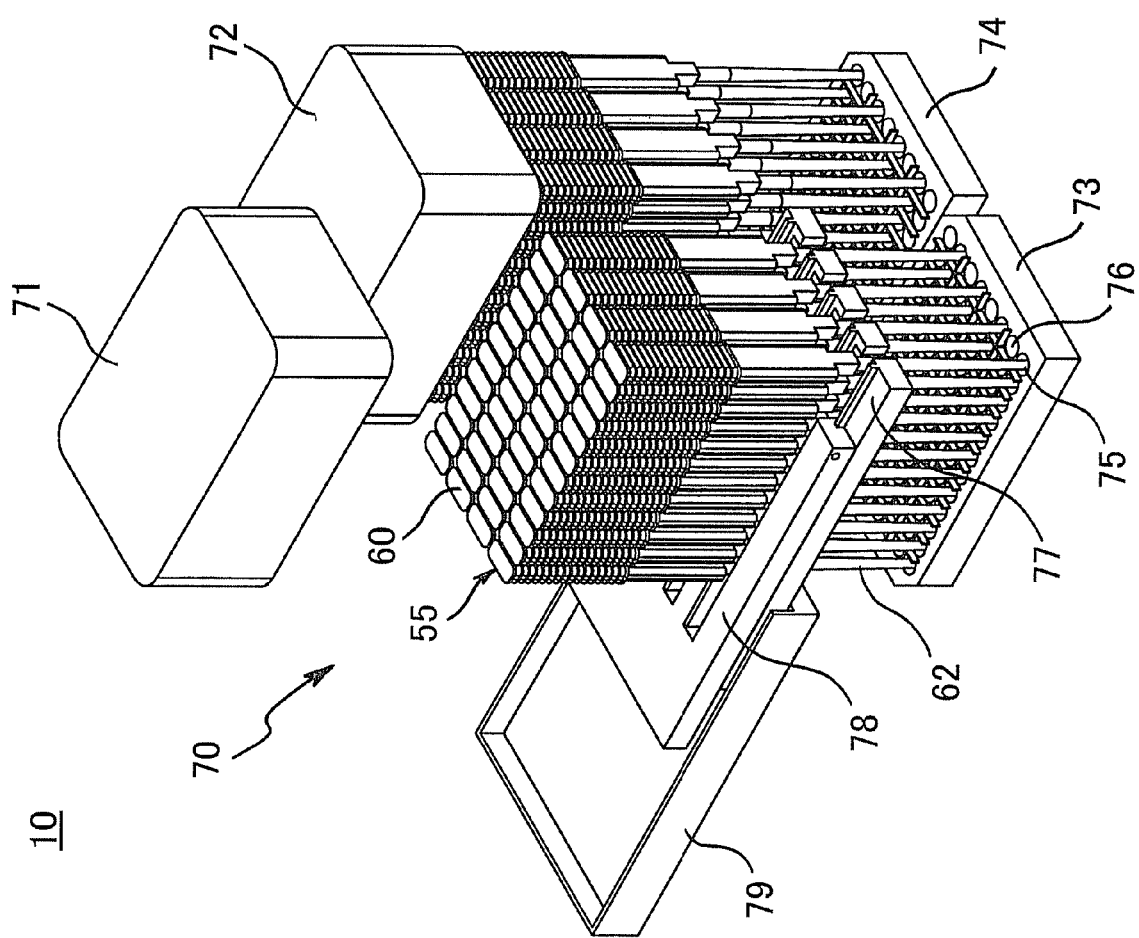
FIG. 6 is a perspective view of a carrier-enclosed transformable container according to a fifth embodiment of the invention.
Figure 7:
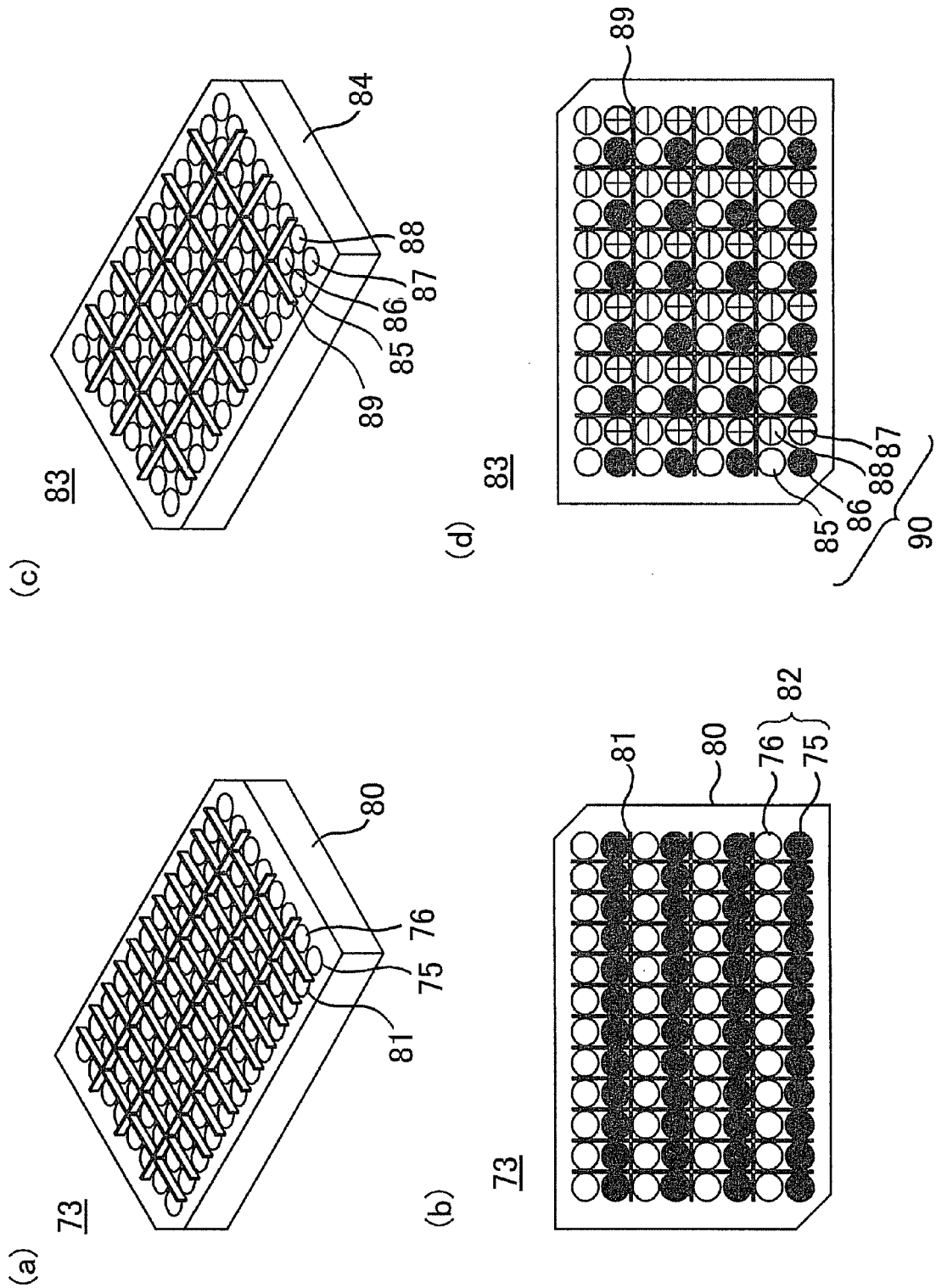
FIG. 7 are each a view illustrating a micro plate of the carrier-enclosed transformable container according to the fifth embodiment of the invention.
Figure 8:
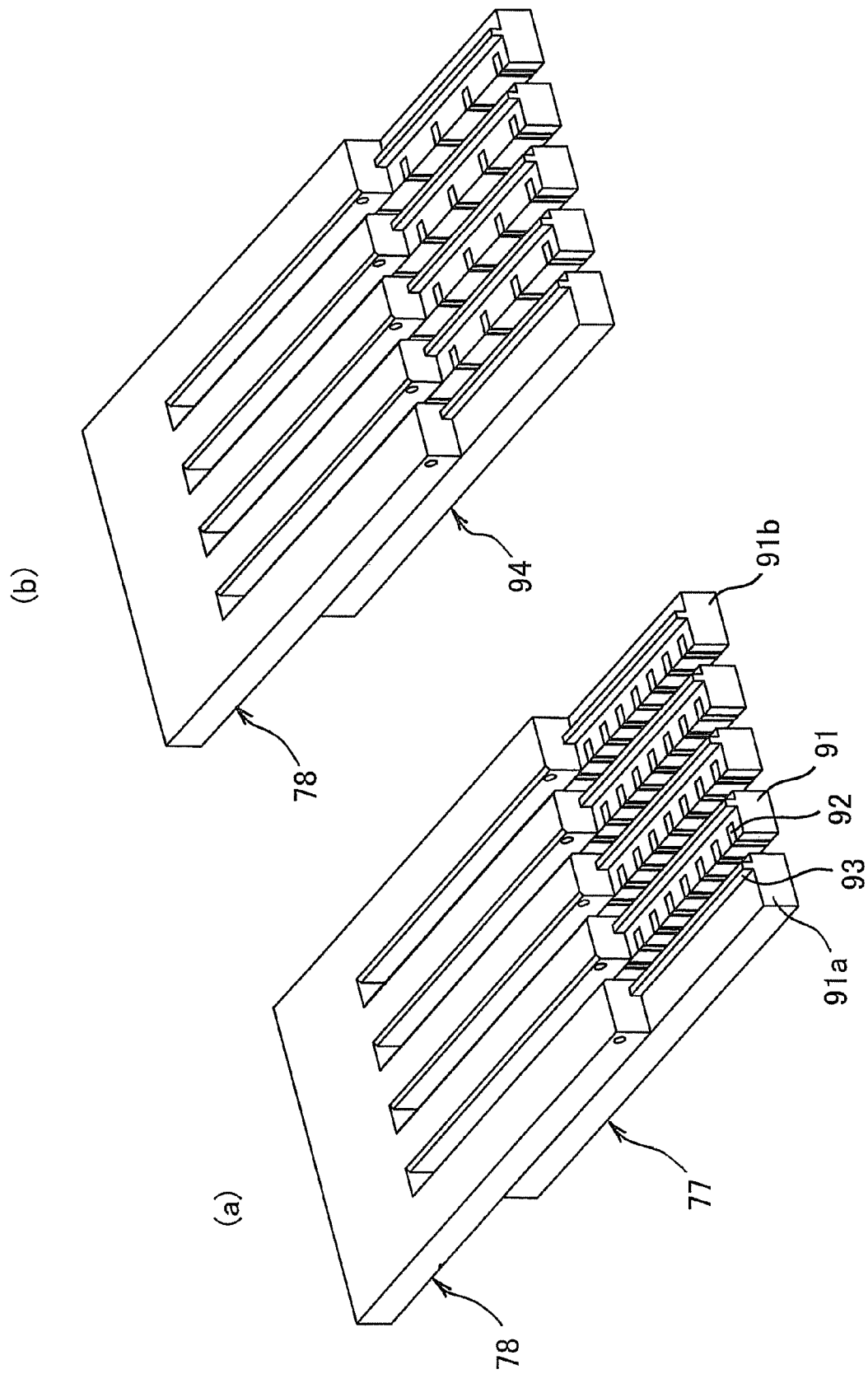
FIG. 8 are each a perspective view illustrating a comb-tooth light-detecting unit and a comb-tooth magnet according to the fifth embodiment of the invention.
Figure 9:
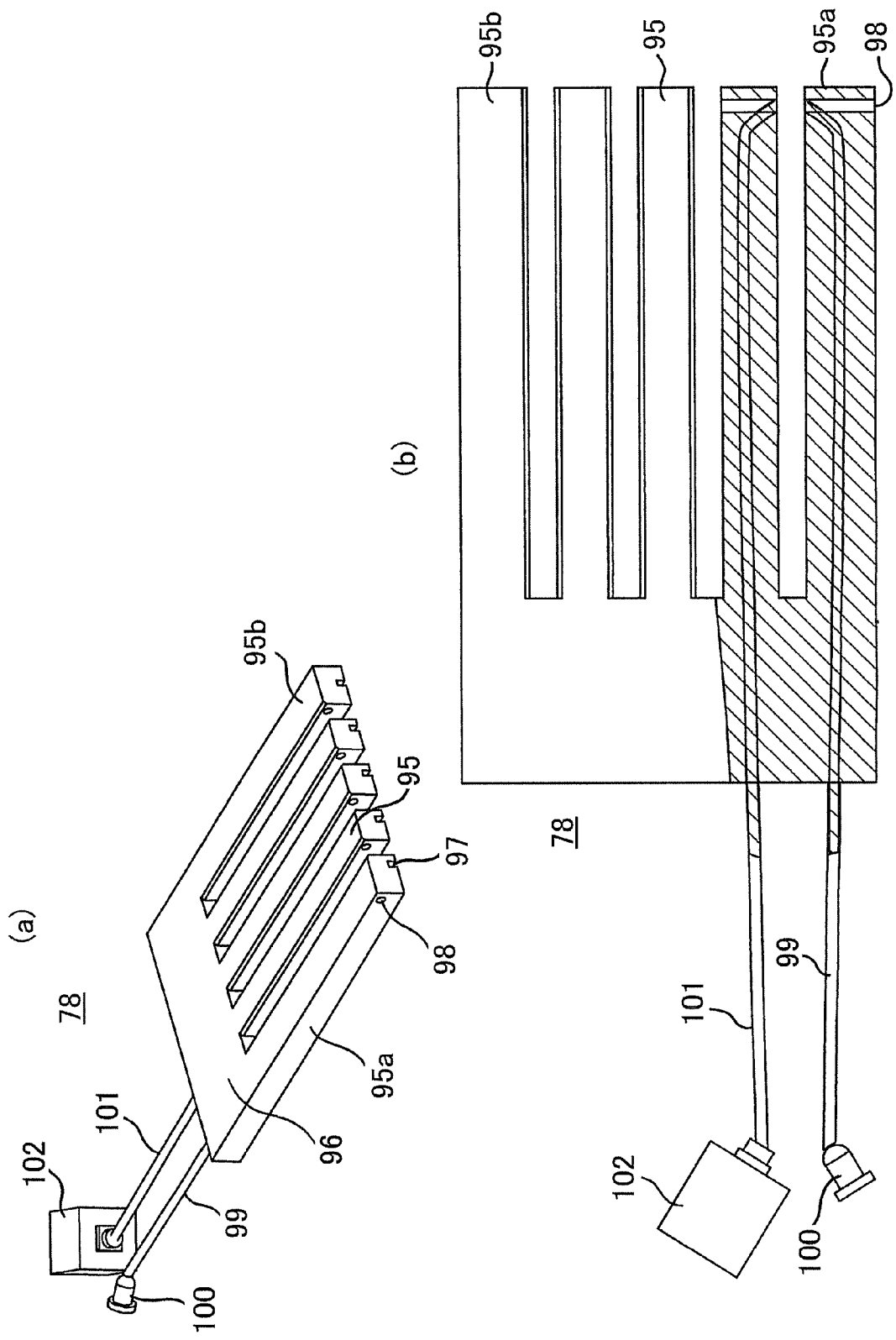
FIG. 9 are views illustrating the comb-tooth light-detecting unit according to the fifth embodiment of the invention.
Figure 10:
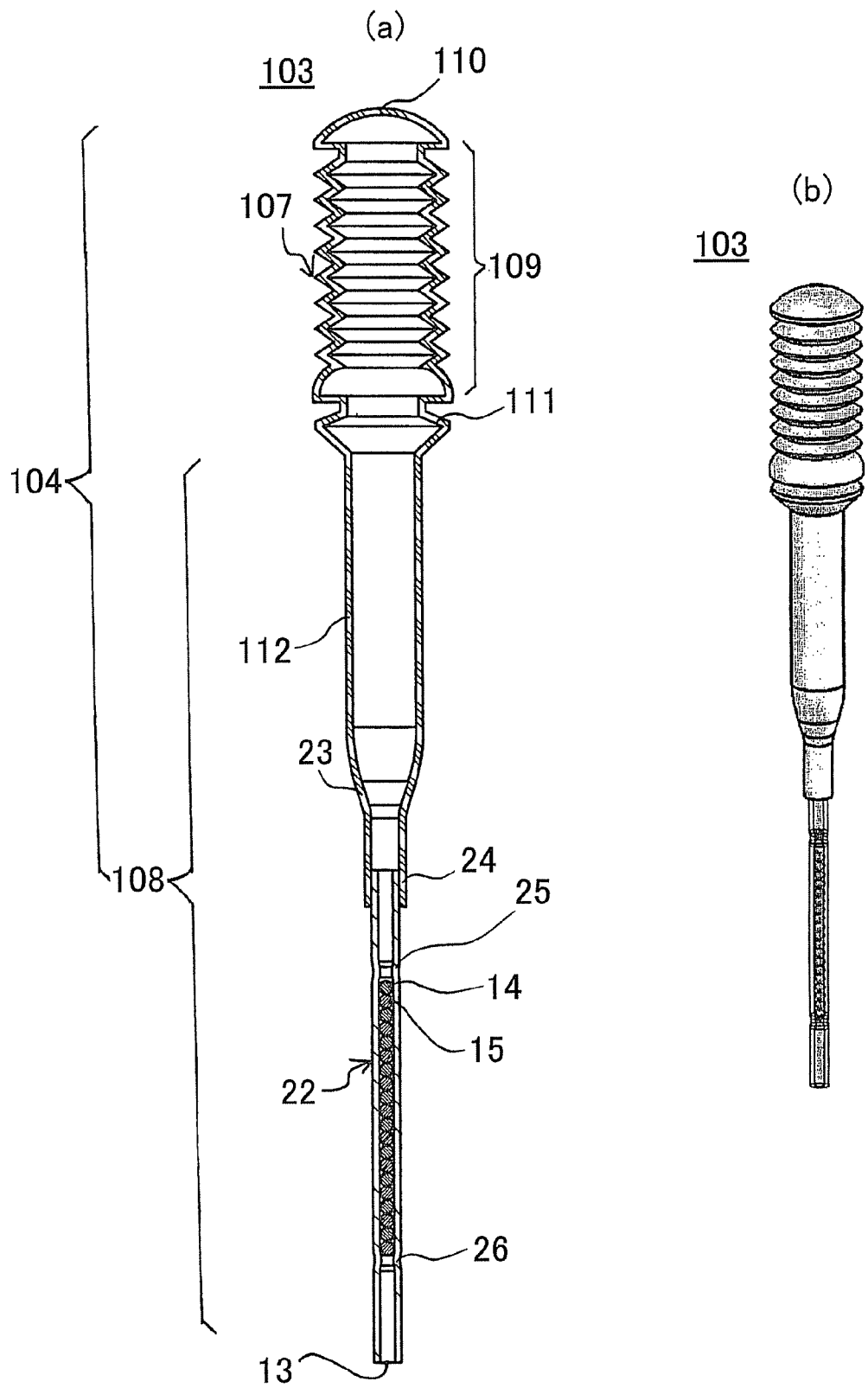
FIG. 10 are a sectional view and a perspective view illustrating a carrier-enclosed transformable container according to a sixth embodiment of the invention.
Figure 11:
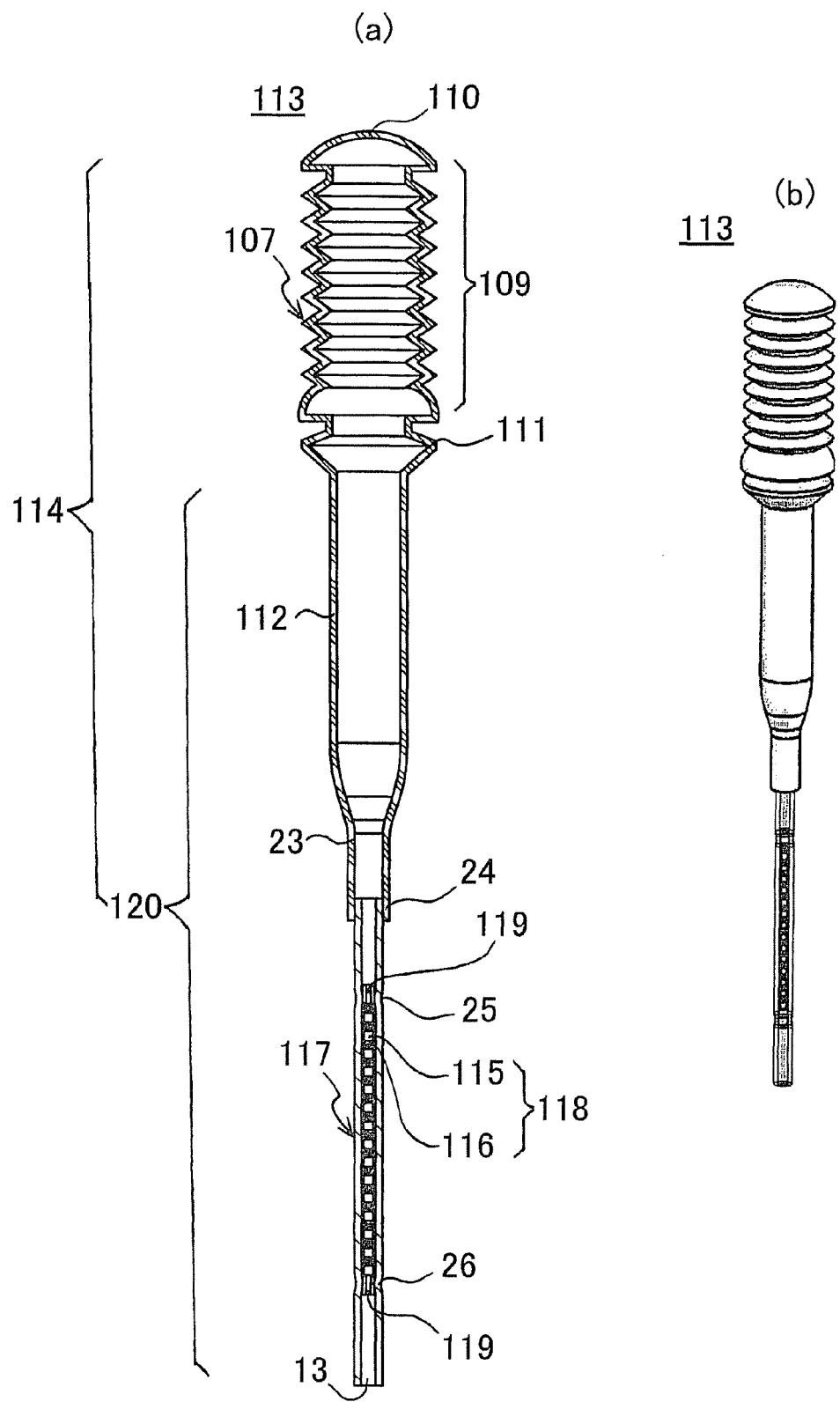
FIG. 11 are a sectional view and a perspective view illustrating a carrier-enclosed transformable container according to a seventh embodiment of the invention.
Figure 12:
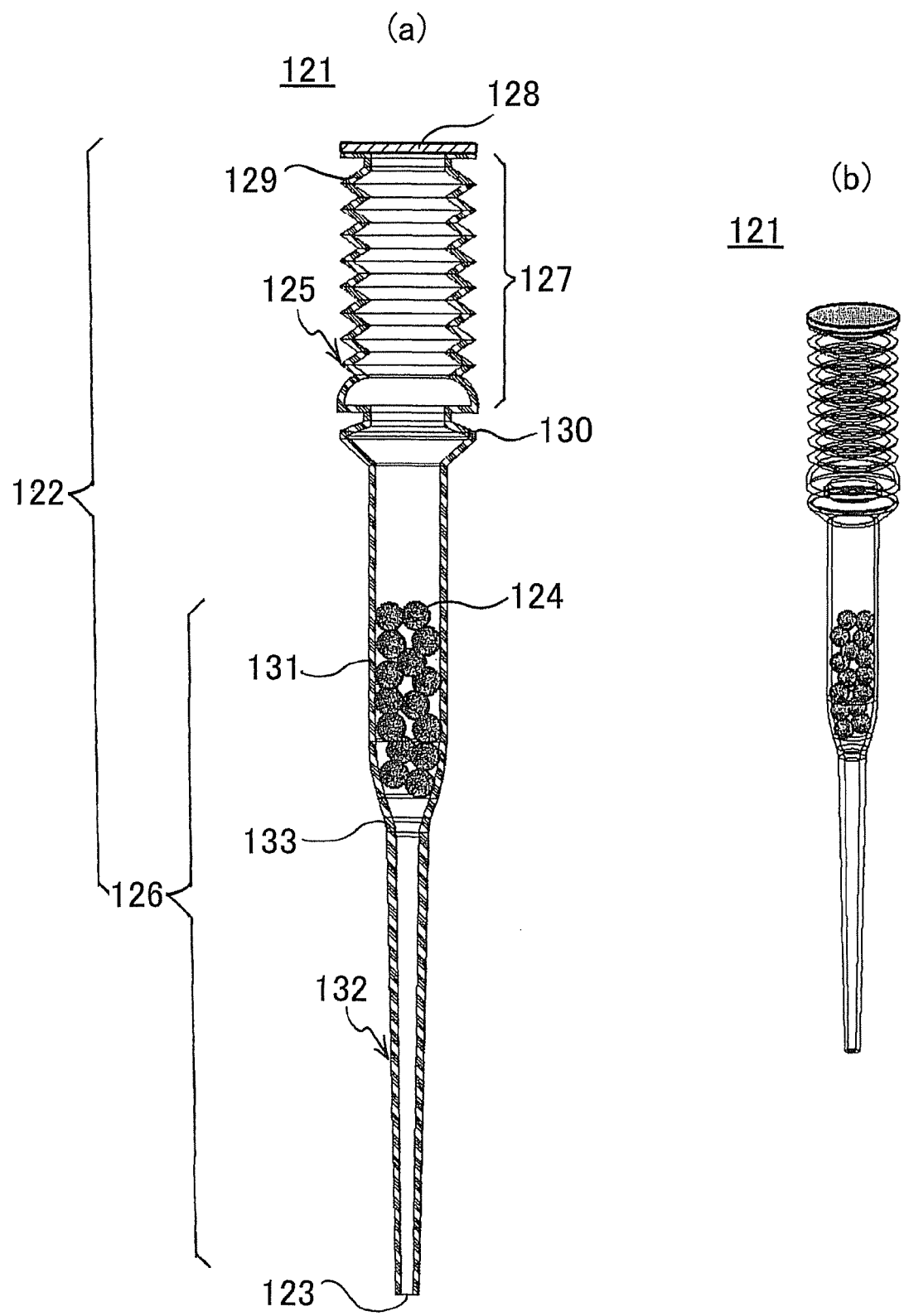
FIG. 12 are a sectional view and a perspective view illustrating a carrier-enclosed transformable container according to an eighth embodiment of the invention.
Figure 13:
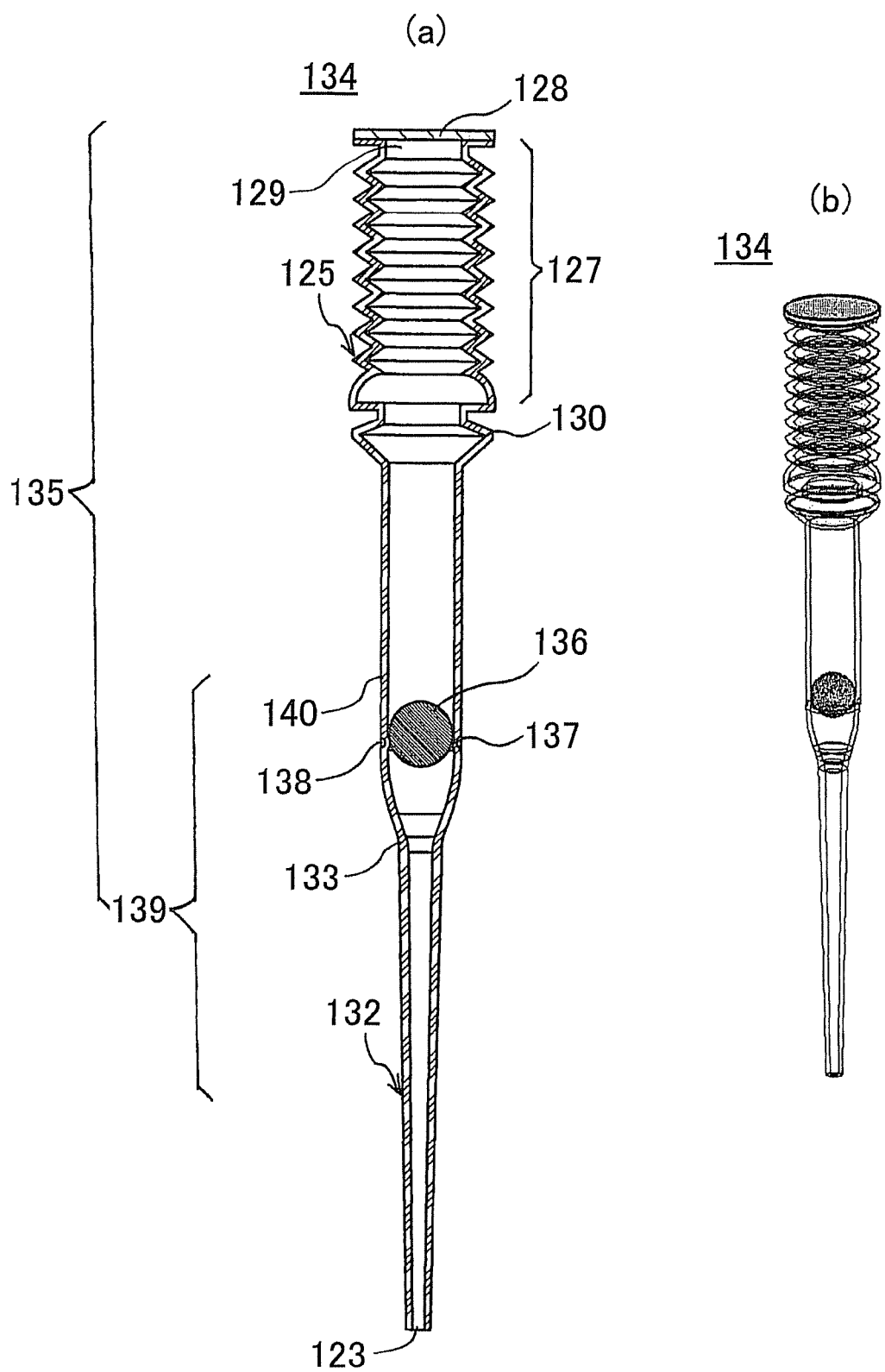
FIG. 13 are a sectional view and a perspective view illustrating a carrier-enclosed transformable container according to a ninth embodiment of the invention.
Figure 14:
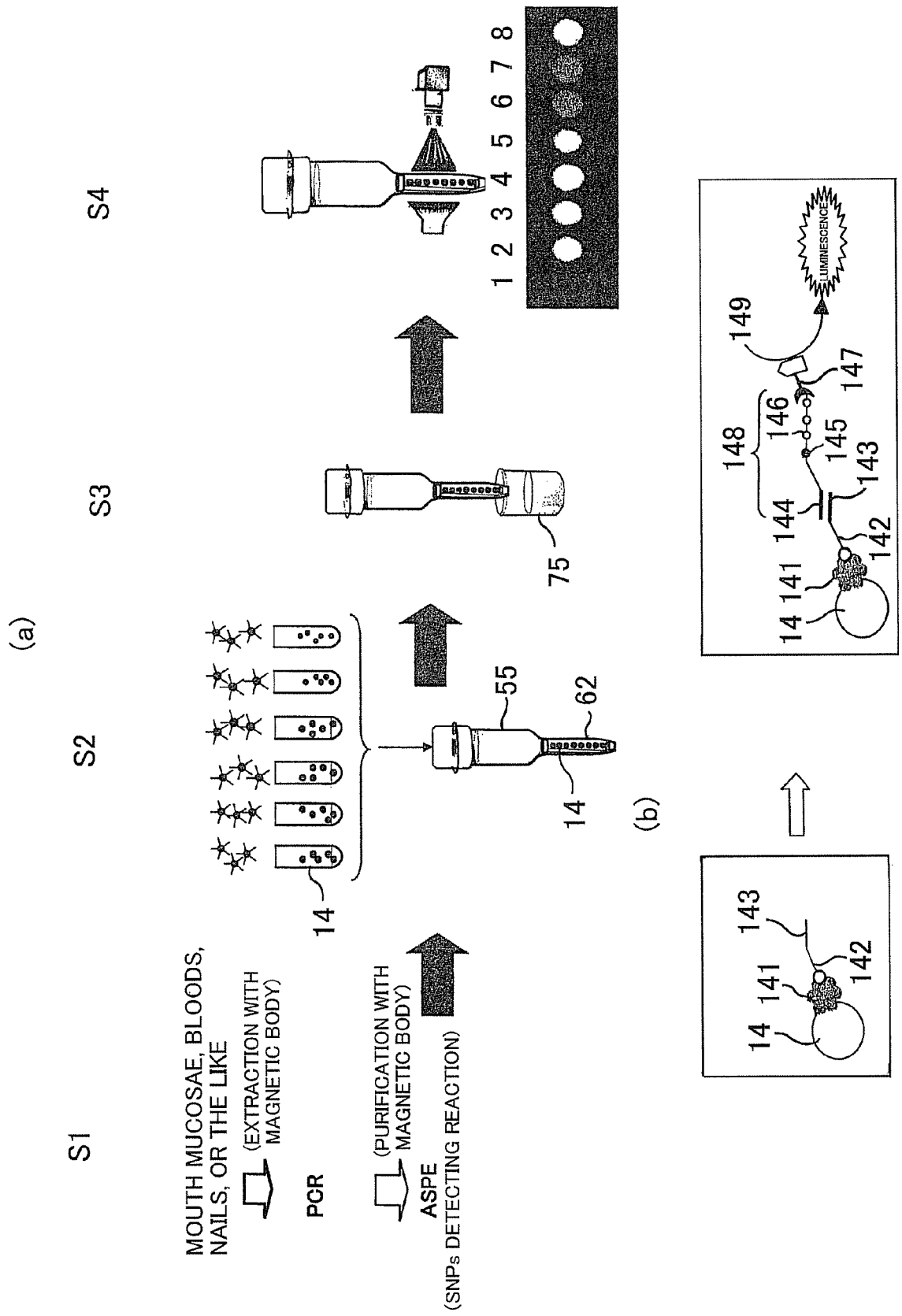
FIG. 14 are a sectional view and a perspective view illustrating a carrier-enclosed transformable container according to a tenth embodiment of the invention.

11, 27, 36, 55, 103, 113, 121, and 134 carrier-enclosed transformable containers

14, and 15 carrier particles

18, 59, 109, and 127 bellows

70 carrier enclosed head

The invention claimed is:

1. A carrier-enclosed transformable container having: containing part which can contain liquid and gas at its inside surrounded by a wall face, a part of this wall face having a transformable wall face capable of undergoing a predetermined transformation without changing the entire internal surface area of the wall face substantially; an orifice part which is connected to the containing part at an end thereof opposite the transformable wall face and which can undergo the inflow and outflow of a fluid sucked and discharged by the expansion and contraction of the inside by the transformation of the transformable wall face, respectively; a carrier to which a predetermined substance enclosed in the containing part to be in a substantially stationary state is bonded or bondable, and an enclosing portion for enclosing the carrier into the containing part in the state that the carrier can contact a fluid flowing from the orifice part to the containing part; wherein positions where the substance is bonded or bondable are caused to correspond to predetermined positions of an individual of the carrier at intervals, or to correspond to plural individuals of the carrier, and about the carrier, its positions to which the predetermined substance is bonded or bondable can be specified from the outside, wherein the containing part has one or more transformable portions formed by the transformable wall face, and a non-transformable portion connected to the transformable portion(s), and surrounded by a non-transformable wall face, which is not transformable, and is also connected to the orifice part, the inside of the non-transformable portion being permitted to be measured from the outside, and wherein the enclosing portion is part of the non-transformable portion and thus the carrier is enclosed in the non-transformable portion;

wherein the orifice part has a size that permits the carrier to pass through the orifice part in a direction that corresponds to a flow direction in which the fluid is sucked into the opening part and flows through the opening and the enclosing portion; and wherein either:

the enclosing portion has a carrier-passage-blocking member arranged so that the fluid can pass out of the enclosing portion in the flow direction but the carrier cannot pass out of the enclosing portion in the flow direction, the carrier-passage-blocking member being positioned to separate the carrier from the transformable portion(s) along the flow direction, or the containing part has a projected region formed by the non-transformable wall face projecting in a direction perpendicular to the flow direction so that the fluid can pass out of the enclosing portion in the flow direction but the carrier cannot pass out of the enclosing portion in the flow direction, the projected region being positioned to separate the carrier from the transformable portion(s) along the flow direction.

2. The carrier-enclosed transformable container according to claim 1, wherein the containing part has at least two of the transformable portions, and is formed to make the following different from each other: the maximum variable volumes based on transformations of the transformable wall faces of the individual transformable portions, and the transformable portions are connected to each other through the non-transformable portion.

3. The carrier-enclosed transformable container according to claim 1, wherein the carrier is made of plural carrier particles or plural carrier particle groups to which plural chemical substances are bonded or bondable, the particles or the groups being capable of being distinguished from the outside.

4. The carrier-enclosed transformable container according to claim 1, wherein the non-transformable portion has a thick-tube portion which can store liquid therein, a thin-tube portion or thin-layer portion which is thinner than the thick-tube portion, and a transition portion connected to the thick-tube portion and the thin-tube portion or thin-layer portion and arranged between the thick-tube portion and the thin-tube portion or thin-layer portion, the orifice part is located to be connected to the thin-tube portion or thin-layer portion, and the carrier is enclosed in the thin-tube portion or the thin-layer portion.

5. The carrier-enclosed transformable container according to claim 1, wherein the enclosing portion has an introducing hole made in the wall face of the containing part so as to permit the carrier to be introduced into the containing part, and a cover for covering the introducing hole.

6. The carrier-enclosed transformable container according to claim 1, wherein a region into which the carrier is enclosed, in the non-transformable portion, is set to be freely attached and removed.

7. The carrier-enclosed transformable container according to claim 1, wherein a bellows is formed in the transformable wall face.

8. A carrier-enclosed transformable container processing apparatus having:

two or more carrier-enclosed transformable containers each having a containing part which can contain liquid and gas at its inside surrounded by a wall face, a part of this wall face having a transformable wall face capable of undergoing a predetermined transformation without changing the entire internal surface area of the wall face substantially; an orifice part which is connected to the containing part at an end thereof opposite the transformable wall face and which can undergo the inflow and outflow of a liquid sucked and discharged by the expansion and contraction of the inside by the transformation of the transformable wall face, respectively, a carrier to which a predetermined substance enclosed in the containing part to be in a substantially stationary state is bonded or bondable, and an enclosing portion for enclosing the carrier into the containing part in the state that the carrier can contact a fluid flowing from the orifice part to the containing part; and one or more carrier enclosed heads for supporting the carrier-enclosed transformable containers at respective non-transformable portions thereof in the manner that the orifice parts are not changed or moved by the deformation of the respective transformable wall faces, and causing the respective transformable wall faces of the carrier-enclosed transformable containers to be transformed, thereby sucking a liquid into the carrier-enclosed transformable containers and discharging the liquid therefrom, wherein positions where the substance is bonded or bondable are caused to correspond to predetermined positions of an individual of the carrier at intervals, or to correspond to plural individuals of the carrier, and the carrier is enclosed in the manner that its positions to which the predetermined substance is bonded or bondable can be specified from the outside, and further the carrier enclosed head(s) (each) has/have a carrier containing part supporting portion which can support the two or more carrier-enclosed transformable containers, and movable members which can simultaneously advance and retreat along a predetermined transformable direction of the transformable wall face of the carrier-enclosed transformable containers, wherein each of the containing parts has one or more transformable portions formed by the transformable wall face, and the corresponding non-transformable portion is connected to the transformable portion(s), and surrounded by a non-transformable wall face, which is not transformable, and is also connected to the corresponding orifice part, the inside of the corresponding non-transformable portion being permitted to be measured from the outside, and wherein the enclosing portion is part of the non-transformable portion and thus the carrier is enclosed in the non-transformable portion.

9. The carrier-enclosed transformable container processing apparatus according to claim 8, which further has a holder group having plural holders in which various liquids such as various solutions or suspensions can be held, and a head moving unit for moving (each of) the carrier enclosed head(s) to the holder group, wherein the individual holders set in the holder group are located in the manner that the orifice parts can be simultaneously inserted.

10. The carrier-enclosed transformable container processing apparatus according to claim 8, wherein (each of) the carrier enclosed head(s) is provided with a magnetic force means having two or more magnets set to the containing parts so as to be brought into contact with and separated from the containing parts in the manner that a magnetic field can be simultaneously applied to the containing parts and can further be removed,
- wherein a plurality of wells are arranged in a matrix form having a first row interval and a first column interval;
- wherein the two or more carrier-enclosed transformable containers are arranged in a number of orifice part rows or a number of orifice part columns, the number of orifice part rows having a second row interval and the number of orifice part columns having a second column interval, the second row interval or the second column interval corresponding to a natural number multiple of the first row interval or the first column interval, respectively;
- wherein the magnetic force means has comb-tooth members that are arranged between the number of orifice part rows or the number of orifice part columns so as to be permitted to be relatively moved in the orifice part row direction or the orifice part column direction, respectively;
- wherein each of the comb-tooth members extends along the orifice part row direction or the orifice part column direction and each of the comb-tooth members has a width permitted to be inserted in between the number of orifice part rows or the number of orifice part columns, the comb-tooth members have a supporting member connected to the comb-tooth members; and
- wherein each of the comb-tooth members is provided with a number of magnets arranged at positions corresponding to the second column interval or the second row interval, the number of the magnets equal to the number of orifice part rows or to the number of orifice part columns.

11. The carrier-enclosed transformable container processing apparatus according to claim 8, wherein (each of) the carrier enclosed head(s) further has a photodetector for detecting the state of the containing parts
- wherein a plurality of wells are arranged in a matrix form having a first row interval and a first column interval;
- wherein the two or more carrier-enclosed transformable containers are arranged in a number of orifice part rows or a number of orifice part columns, the number of orifice part rows having a second row interval and the number of orifice part columns having a second column interval, the second row interval and the second column interval corresponding to a natural number multiple of the first row interval or the first column interval, respectively;
- wherein the photodetector has comb-tooth members that are arranged between the number of orifice part rows or the number of orifice part columns so as to be permitted to be relatively moved in the orifice part row direction or the orifice part column direction, respectively;
- wherein each of the comb-tooth members extends along the orifice part row direction or the orifice part column direction and each of the comb-tooth members has a width permitted to be inserted in between the number of orifice part rows or the number of orifice part columns, the comb-tooth members have a supporting member connected to the comb-tooth members; and
- wherein each of the comb-tooth members is provided with a photo-detecting unit.

12. The carrier-enclosed transformable container processing apparatus according to claim 9, which has a control unit for controlling the transformation of the transformable wall, and/or movement between the carrier enclosed head(s) and the holder groups on the basis of the number or the structure of the carrier-enclosed transformable containers; a liquid to be sucked and discharged, a substance contained therein, the amount thereof, the containing position thereof, the temperature thereof or the concentration thereof; the content of a processing; or instructions.

13. The carrier-enclosed transformable container processing apparatus according claim 8, wherein about the transformation of the transformable wall face, a predetermined standard position is set, and the transformation of the transformable wall face is controlled with reference to the standard position.

14. The carrier-enclosed transformable container processing apparatus according to claim 8, wherein the orifice part is located at a lower end thereof, the containing part is located over the orifice part, a part of the wall face surrounding the containing part has the transformable wall face transformable in the vertical direction so as to partition the inner wall face into upper and lower regions, the upper end of the containing part and the movable member are set to be brought into contact with each other or connected to each other.

* * * * *